United States Patent
O'Neill

(10) Patent No.: US 6,630,467 B2
(45) Date of Patent: *Oct. 7, 2003

(54) PYRIDONE-FUSED AZABICYCLIC- OR CYTISINE DERIVATIVES, THEIR PREPARATION AND THEIR USE IN ADDICTION THERAPY

(75) Inventor: Brian T. O'Neill, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,443

(22) Filed: Feb. 14, 2001

(65) Prior Publication Data

US 2003/0065173 A1 Apr. 3, 2003

Related U.S. Application Data

(62) Division of application No. 09/297,109, filed as application No. PCT/IB97/01282 on Oct. 15, 1997, now Pat. No. 6,235,734.
(60) Provisional application No. 60/028,804, filed on Oct. 30, 1996.

(51) Int. Cl.[7] .............. A61K 31/4375; A61K 31/5377; C07D 431/18; C07D 471/08; C07D 413/04; A61P 25/30
(52) U.S. Cl. ............... 514/233.2; 514/292; 544/126; 546/81
(58) Field of Search .................. 546/81; 514/292, 514/233.2; 544/126

(56) References Cited

U.S. PATENT DOCUMENTS

| | | |
|---|---|---|
| 4,835,162 A | 5/1989 | Abood |
| 5,242,916 A * | 9/1993 | Lippiello .................. 514/214 |

FOREIGN PATENT DOCUMENTS

| | | |
|---|---|---|
| WO | WO 8302892 | 9/1983 |
| WO | WO 9511678 | 5/1995 |
| WO | WO 97/11072 * | 3/1997 |

OTHER PUBLICATIONS

Orjales A et al. An. Quim. (1972), 68(12), 1419–32.*
Luputiu G et al. Arch. Pharm. (Weinheim) (1971), 304(2), 151–8.*
Partheil A.; Uber Cytisin und Ulexin; vol. 232, 1894, pp. 161–177.
Lammers J.; Beitrage zur Kenntnis des Cytisins; vol. 235, 1897, pp. 374–397.
Wink M. et al.; Patterns of quinolizidine alkaloids in 56 species of the genus lupinus; vol. 38, No. 1, (1995); pp. 139–153.
Talapin V.I., et al.; Chemical Abstract; Pharmaceuticals as smoking deterrents; vol. 99, No. 26. (1983).
Iskanderov S., et al.; Dimethamine—a new bimolecular alkaloid; Chemistry of Natural Compounds: vol. 8, (1972); p. 216–218.

* cited by examiner

Primary Examiner—Evelyn Mei Huang
(74) Attorney, Agent, or Firm—P. C. Richardson; S. Drouin; A. D. Joran

(57) ABSTRACT

Pyridone-fused azabicyclic compounds of the formula

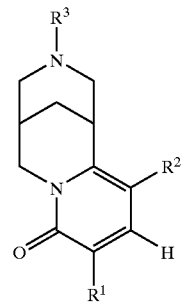

and their pharmaceutically acceptable salts and prodrugs, wherein $R^1$, $R^2$ and $R^3$ are defined below, intermediates and methods for their preparation. Compositions and methods for using compounds of the formula I in the treatment of neurological and mental disorders related to a decrease in cholinergic function such as nicotine addiction, Huntington's Chorea, tardive dyskinesia, hyperkinesia, mania, dyslexia, schizophrenia, analgesia, attention deficit disorder (ADD), multi-infarct demetia, age related cognitive decline, epilepsy, neurological and mental disorders related to a decrease in cholinergic function, senile dementia of the Alzheimer's type, Parkinson's disease, attention deficit hyperactivity disorder (ADHD), anxiety, obesity, Tourette's Syndrome and ulcerative colitis.

15 Claims, No Drawings

US 6,630,467 B2

PYRIDONE-FUSED AZABICYCLIC- OR CYTISINE DERIVATIVES, THEIR PREPARATION AND THEIR USE IN ADDICTION THERAPY

This application claims priority under 35 U.S.C. §120 as a divisional of application Ser. No. 09/297,109, filed Jun. 11, 1999 now U.S. Pat. No. 6,235,734, which is a 35 U.S.C. §371 filing of PCT application PCT/IB97/01282, filed Oct. 15, 1997, which claims priority under 35 U.S.C. §119(e) of U.S. application Serial No. 60/028,804, filed Oct. 30, 1996, which applications are hereby incorporated by reference herein.

BACKGROUND OF THE INVENTION.

This invention relates to azabicyclic compounds. More particularly it relates to pyridone-fused azabicyclic compounds of the formula I below Compounds of formula I are useful in the treatment of addictive disorders such as the use of tobacco or other nicotine containing products and also for the treatment or prevention of withdrawal symptoms caused by cessation of chronic or long term use of tobacco products. These compounds are also useful in the treatment of Huntington's Chorea, tardive dyskinesia, hyperkinesia, mania, dyslexia, schizophrenia, analgesia, attention deficit disorder (ADD), multi-infarct demetia, age related cognitive decline, epilepsy, neurological and mental disorders related to a decrease in cholinergic function such as Huntington's Chorea, tardive dyskinesia, hyperkinesia, mania, dyslexia, schizophrenia, analgesia, attention deficit disorder (ADD), multi-infarct demetia, age related cognitive decline, epilepsy, neurological and mental disorders related to a decrease in cholinergic function, senile dementia of the Alzheimer's type, Parkinson's disease, attention deficit hyperactivity disorder (ADHD), anxiety, obesity, Tourette's Syndrome and ulcerative colitis.

The compounds of this invention may also be used in combination with a anti-depressants such as imipramine in order to treat both the cognitive decline and depression associated with AD; in combination with serotonin uptake inhibitors such as Zoloft to treat both the cognitive decline and depression associated with AD; in combination with muscarinic agonists in order to stimulate both central muscarinic and nicotinic receptors; in combination with neurotrophic factors such as NGF in order to maximize cholinergic enhancement; in combination with agents which slow or arrest AD such as amyloid or tau inhibitors.

Substances which can deliver pharmacologically relevant amounts of nicotine to the central nervous system are among the most abused substances known. These include, but not are not limited to tobacco cigarettes, and "chewing tobacco" (see J. E. Henningfield, Ph.D, *New England Journal of Med.*, 1196, 1995). Cigarette smoking has been tied to increased risk for lung cancer, emphysema and heart disease and it is estimated 400,000 people will die in 1995 from the combined effects of nicotine abuse in the United States (see J. A. Califano, Jr., *New England Journal of Med.* 1214, 1995). Nicotine is a highly addicting drug with 40% of those who try smoking later becoming physically dependent upon it. Attempts to quit the use of nicotine, such as in smoking, have been largely ineffective with >80% of such attempts ending in failure. Most attempts to quit end in failure in the first week due to intense withdrawal and craving symptoms. An effective therapy should aid in the cessation or lessening of tobacco use, prevent withdrawal, etc. prevent withdrawal symptoms, relieve craving and, simultaneously, antagonize the reinforcing effects of nicotine obtained through smoking. Currently, few therapies are available for smoking cessation and most involve replacement of cigarettes with nicotine in the form of a patch or gum. A high rate of relapse and low overall success in ending nicotine use is evidence of the need for additional and more effective therapies for treatment of nicotine addiction than the nicotine patch or gum.

Pharmaceutical compositions employed for the treatment of chronic nicotinism and addiction to nicotine can be divided into two groups The first covers salts of silver, iron and copper. These substances are employed to develop a negative reflex to smoking usually in the form of a solution, or by incorporation in chewing gum compositions. The resultant reflex is based on the appearance of a strong unpleasant taste in the mouth during smoking after a preliminary rinsing of the mouth cavity with solutions of salts, or after the use of a chewing gum containing such salts (See Nasirov a al. "*Anabasine Hydrochloride—New Antismoking Agent*", *Chemico-Pharmaceutical Journal, vol XII,* 1978, No. 2, 149–152).

The second group of agents that are used for the suppression of nicotine addition comprises substances of an alkaloidal nature, such as 1,2,3,4,5,6-hexahydro-1,5-methano-pyrido[1,2-a][1,5]diazocin-8-one (hereafter cytisine), lobeline and anabasine hydrochloride, possessing an effect on H-cholinoreactive systems of the organism similar to that of nicotine. The mechanism of their effect is due to their structural similarity with nicotine and the possible "competitive" antagonism between these alkaloids and nicotine (F. R. Khalikova, S. H. Nasirov, "*On pharmacology of the Alkaloid Anabasine and some Polymeric and Copolymeric Derivatives Thereof*", in Coll. "*Pharmacology of Vegetable Compounds*", *Proceedings of Tashkent University,* 457, 1973, 5–16).

U.S. Pat. No. 4,971,079 describes a composition comprising a biologically resorbable polymer containing a cation exchange group modified by an antinicotine action alkaloid, such as anabasine or cytisine, and a gum containing same. However, it has been found that the potency of cytisine is not high due to its inability to penetrate the brain barrier. (Reavill. C. et al., *Behavioural and Pharmacokinetic Studies On Nivotine Cytisine and Lobeline, Neuropharmacology,* 29, 619–624 (1990)). Labadie L. C. ((*Peut-on supprimer les facteurs de risque en bronchopatie chronique et en particulier le tabac*", *Mediater, med,* 1976, 4, No. 112, 97, 99)) describes the use of leaves of other night-shade plants, such as potato, tomato, eggplant and digitalis as tobacco substitutes.

One of the most successful approaches to date in reducing the incidence of smoking relies upon nicotine containing chewing gum which is designed to reduce smoking withdrawal symptoms. The reported success rate, while still relatively low, is approximately twice that of the other methods which have heretofore been employed. (See *British Medical Journal,* 286, (1983)).

The use of the nicotine gum suffers from several problems including bad taste, destruction of dental appliances and gastrointestinal discomfort thereby reducing their use to suppress nicotine addiction. In addition, it has been found that the nicotine containing gum does not completely satisfy the craving that most smokers experience for nicotine and often nicotine gum becomes addictive to the patient.

A simulated smoking device which uses a source of vaporizable nicotine is claimed in U.S. Pat. No 4,284,089 While the cigarette itself is non-combustible it delivers a nicotine-containing vapor which may not raise the nicotine level in the blood sufficiently to satisfy a smoker Thus, it has not been shown to satisfy the desire for a certain nicotine level in the blood to which many smokers have become accustomed and, even more so, upon which many smokers have become dependent. In addition, the simulated smoking devices of the type taught in U.S. Pat. No. 4,284,089 also suffer from the bad taste of a substantial amount of nicotine introduced into the oral cavity. More importantly, this nicotine does not penetrate into the chest for stimulating and providing that sensation normally provided by nicotine and to which the smoker has become accustomed.

The current first line therapy for smoking cessation, as described in U.S. Pat. No. 5,016,652 describes a transdermal patch which is useful for the controlled delivery of nicotine to the bloodstream of the user thereby reducing the incidence of smoking. Clinical trials have shown that abstinence rates (with the nicotine patch) of 30 to 40% can be achieved during the first six weeks of application (K. J. Palmer, M. M. Buckley, D. Faulds, Drugs 44(3) 498–529, (1992) compared with 4 to 21% with a placebo. However, long term abstinence rates (>6 months) are considerably lower, falling to between 11–18%. Thus, a more effective therapy which will afford a greater percentage of smokers who are able to quit is clearly needed.

SUMMARY OF THE INVENTION.

This invention relates to pyridone-fused azabicyclic compounds of the formula

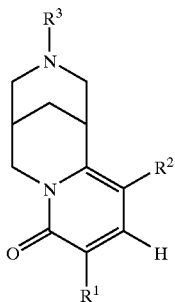

I its enantiomers, diastereomers and stereoisomers, and their pharmaceutically acceptable salts and prodrugs, wherein $R^1$ and $R^2$ are each independently selected from a) H, halo, $CF_3$, hydroxy, $(C_1–C_6)$alkoxy, $CH_2OH$, —C(O)R wherein R=H, $(C_1–C_6)$ alkyl, aryl and benzyl including substituted alkyl, aryl and benzyl, C≡—N, C≡—CR, wherein R=H, $(C_1–C_6)$ alkyl, aryl including substituted alkyl, aryl. —S(O)$_n$R, wherein R=H, $(C_1–C_6)$ alkyl, aryl including substituted alkyl, aryl and n=0, 1, 2. $(C_1–C_6)$alkyl, $(C_1–C_6)$alkenyl, $H_2N$, di-[$(C_1–C_6)$alkyl]amino, $(C_1–C_6)$monoalkylamino, $(C_6–C_{10})$arylamino, $(C_3–C_8)$cycloalkylamino, heteroarylamino, cycloheteroalkyamino and $CON(R^5)_2$ wherein each $R^5$ is selected from hydrogen, $(C_1–C_8)$ alkyl and $(C_6–C_{10})$aryl; and b) $CO_2R$ wherein R is selected from H, $(C_1–C_6)$alkyl, phenyl and benzyl; and c) optionally benzene-fused $(C_6–C_{10})$aryl, optionally benzene-fused $(C_3–C_8)$cycloalkyl, optionally benzene-fused heteroaryl and optionally benzene-fused cycloheteroalkyl, wherein said heteroaryl group contains five to ten atoms comprising one to four heteroatoms, said cycloheteroalkyl contains 4 to 8 atoms comprising one or two heteroatoms selected from N, S and O;

and wherein any of the alkyl, alkenyl, aryl, cycloalkyl, cycloheteroalkyl and heteroaryl groups in a), b) and c) are optionally substituted with one or more substituents selected from halogen, $(C_1–C_6)$alkyl, $(C_6–C_{10})$aryl, hydroxy, hydroxymethyl, CHO and $CO_2R$ wherein R is as described above; and $R^3$ is selected from H, optionally substituted benzyl and methyl;

with the provisos that $R^1$ and $R^2$ are not both hydrogen and when $R^3$ is H, then $R^1$ and $R^2$ when selected from H, Br and Cl, cannot be the same.

In the above compounds, "aryl" includes, without limitation, optionally substituted phenyl and naphthyl, "cycloalkyl" includes, without limitation, optionally substituted cyclopentyl and cyclohexyl, and said cycloalkyl group may also be unsaturated, and "heteroaryl" includes, without limitation, thienyl, furyl, pyrano, pyrrolo, imidazolyl, oxazolyl, thiazolyl, tetrazolyl, triazolyl, pyrazinyl and pyridyl, and said "cycloheteroalkyl" includes, without limitation, pyrrolidinyl, piperidinyl tetrahydrofuryl and tetrahydropyrano.

Preferred compounds of formula I are those wherein $R^3$ is selected from H, benzyl or methyl and $R^1$ and $R^2$ are each independently selected from H, halo, $(C_1–C_6)$alkyl, cyano, $(C_6–C_{10})$aryl, $(C_5–C_9)$heteroaryl, $(C_1–C_6)$alkenyl, $(C_2–C_6)$ alkynyl-R and —C(O)R wherein R is H, $(C_1–C_6)$ alkyl, $(C_5–C_{10})$ aryl and $(C_5–C_9)$heteroaryl and amino and mono and di-substituted amino; with the provisos that when $R^3$ is H then $R^1$ and $R^2$ are not both H, Br and Cl and when $R^3$ is benzyl or methyl then $R^1$ and $R^2$ are not hydrogen.

More preferred compounds of formula I are those wherein $R^1$ and $R^2$ are each independently selected from H, ethyl, methyl, phenyl, vinyl, fluoro, bromo, chloro, isopropyl, tert-butyl, trifluoromethyl, acetyl, propanoyl, 2,2-dimethylpropanoyl, 2-methylpropanoyl, butanoyl, pentanoyl, cyano, di-[$(C_1–C_6)$alkyl]amino, $(C_1–C_6)$ monoalkylamino, $(C_6–C_{10})$arylamino, $(C_3–C_8)$ cycloalkylamino, heteroarylamino, cycloheteroalkyamino and $CON(R^5)_2$ wherein each $R^5$ is selected from hydrogen, $(C_1–C_6)$alkyl and $(C_6–C_{10})$aryl; $(C_6–C_{10})$aryl and $(C_5–C_9)$ heteroaryl wherein the aryl and heteroaryl groups are optionally substituted with one or more substituents selected from halogen, $(C_1–C_6)$alkyl, $(C_6–C_{10})$aryl, hydroxy, hydroxymethyl, CHO and $CO_2R$.

More preferred compounds of formula I are those wherein $R^3$ is selected from optionally substituted benzyl or $(C_1–C_6)$ alkyl, wherein the substituents are described above and $R^1$ and $R^2$ are each independently selected from hydrogen, halo, cyano, optionally substituted $(C_1–C_6)$alkyl, $(C_1–C_6)$alkenyl, amino, di-[$(C_1–C_6)$alkyl]amino, $(C_1–C_6)$monoalkylamino, $(C_6–C_{10})$arylamino, $(C_3–C_8)$cycloalkylamino, heteroarylamino, cycloheteroalkyamino and $CON(RS)_2$ wherein each $R^5$ is selected from hydrogen, $(C_1–C_6)$alkyl and $(C_6–C_{10})$aryl; —C(O)R wherein R is H, $(C_1–C_6)$ alkyl, $(C_5–C_{10})$ aryl and $(C_5–C_9)$heteroaryl; $(C_6–C_{10})$aryl or $(C_5–C_9)$heteroaryl wherein the substituents are described above.

More particularly, the invention relates to compounds of the formula I wherein $R^1$ and $R^2$ are each independently selected from hydrogen isopropyl, tert-butyl, trifluoromethyl, acetyl, propanoyl, 2,2-dimethylpropanoyl, 2-methylpropanoyl, butanoyl, pentanoyl, cyano, 2,4-difluorophenyl, 2-fluorophenyl, 2- and 3-thienyl, dimethylamino and $R^3$ is selected from hydrogen, benzyl, methyl and $R^1$ and $R^2$ are each independently selected from hydrogen, bromo, chloro, ethyl, methyl, fluoro, vinyl and phenyl.

Most preferred compounds of the formula I are selected from
9-bromo-1,2,3,4,5,6-hexahydro-1,5-methano-pyrido[1,2-a][1,5]diazocin-8-one;
11-bromo-1,2,3,4,5,6-hexahydro-1,5-methano-pyrido[1,2-a][1,5]diazocin-8-one;
9-chloro-1,2,3,4,5,6-hexahydro-1,5-methano-pyrido[1,2-a][1,5]diazocin-8-one;
11-chloro-1,2,3,4,5,6-hexahydro-1,5-methano-pyrido[1,2-a][1,5]diazocin-8-one;

9-flouro-1,2,3,4,5,6-hexahydro-1,5-methano-pyrido[1,2-a][1,5]diazocin-8-one;
11-flouro-1,2,3,4,5,6-hexahydro-1,5-methano-pyrido[1,2-a][1,5]diazocin-8-one;
9,11-diflouro-1,2,3,4,5,6-hexahydro-1,5-methano-pyrido[1,2-a][1,5]diazocin-8-one;
9-ethyl-1,2,3,4,5,6-hexahydro-1,5-methano-pyrido[1,2-a][1,5]diazocin-8-one;
11-ethyl-1,2,3,4,5,6-hexahydro-1,5-methano-pyrido[1,2-a][1,5]diazocin-8one;
9,11-diethyl-1,2,3,4,5,6-hexahydro-1,5-methano-pyrido[1,2-a][1,5]diazocin-8-one;
9-methyl-1,2,3,4,5,6-hexahydro-1,5-methano-pyrido[1,2-a][1,5]diazocin-8one;
11-methyl-1,2,3,4,5,6-hexahydro-1,5-methano-pyrido[1,2-a][1,5]diazocin-8-one;
9,11-dimethyl-1,2,3,4,5,6-hexahydro-1,2-methano-pyrido[1,2-a][1,5]diazocin-8-one;
9-phenyl-1,2,3,4,5,6-hexahydro-1,5-methano-pyrido[1,2-a][1,5]diazocin-8-one;
11-phenyl-1,2,3,4,5,6-hexahydro-1,5-methano-pyrido[1,2-a][1,5]diazocin-8-one;
9,11-diphenyl-1,2,3,4,5,6-hexahydro-1,5-methano-pyrido[1,2-a][1,5]diazocin-8-one;
9-vinyl-1,2,3,4,5,6-hexahydro-1,5-methano-pyrido[1,2-a][1,5]diazocin-8-one;
11-vinyl-1,2,3,4,5,6hexahydro-1,5-methano-pyrido[1,2-a][1,5]diazocin-8-one;
9,11-divinyl-1,2,3,4,5,6-hexahydro-1,5-methano-pyrido[1,2-a][1,5]diazocin-8-one;
9-bromo-3-methyl-1,2,3,4,5,6-hexahydro-1,5-methano-pyrido[1,2-a][1,5]diazocin-8-one;
3-benzyl-9-bromo-1,2,3,4,5,6-hexahydro-1,5-methano-pyrido[1,2-a][1,5 ]diazocin-8-one, and
3-benzyl-9-chloro-1,2,3,4,5,6-hexahydro-1,5-methano-pyrido[1,2a][1,5]diazocin-8-one.

Most preferred compounds of the formula I are selected from:
9-morpholino-1,2,3,4,5,6-hexahydro-1,5-methano-pyrido[1,2a][1,5]diazocin-8-one;
9-benzylamino-1,2,3,4,5,6-hexahydro-1,5-methano-pyrido[1,2a][1,5]diazocin-8-one,
9-pyrrolidino-1,2,3,4,5,6hexahydro-1,5-methano-pyrido[1,2a][1,5]diazocin-4-one;
9-dimethylamino-1,2,3,4,5,6-hexahydro-1,5-methano-pyrido[1,2a][1,5]diazocin-8one;
9-acetyl-1,2,3,4,5,6-hexahydro-1,5-methano-pyrido[1,2a][1,5]diazocin-8-one;
9-(2-tetrahydrofuranyl)-1,2,3,4,5,6-hexahydro-1,5methano-pyrido[1,2a][1,5]diazocin-8-one
9-iodo-1,2,3,4,5,6-hexahydro-1,5-methano-pyrido[1,2a][1,5]diazocin-8-one;
9-cyano-1,2,3,4,5,6-hexahydro-1,5-methano-pyrido[1,2a][1,5]diazocin-8-one;
9-ethynyl-1,2,3,4,5,6-hexahydro-1,5-methano-pyrido[1,2a][1,5]diazocin-8-one;
9-(2-propenyl)-1,2,3,4,5,6-hexahydro-1,2-methano-pyrido[1.2a][1,5]diazocin-8-one;
9-(2-propyl)-1,2,3,4,5,6-hexahydro-1,5-methano-pyrido[1,2a][1,5]diazocin-8-one;
9-carbomethoxy-1,2,3,4,5,6-hexahydro-1,5-methano-pyrido[1,2a][1,5]diazocin-8-one;
9-carboxyaldehyde-1,2,3,4,5,6-hexahydro-1,5-methano-pyrido[1,2a][1,5]diazocin-8-one;
9-(2-methoxyphenyl)-1,2,3,4,5,6-hexahydro-1,5-methano-pyrido[1,2a][1,5]diazocin-8-one;
9-(2,6-difluorophenyl)-1,2,3,4,5,6-hexahydro-1,5-methano-pyrido[1,2a][1,5]diazocin-8-one;
9-[2-(1,1,1-trifluoromethylpropenyl)-1,2,3,4,5,6-hexahydro-1,5-methano-pyrido[1,2a][1,5]diazocin-8-one;
9-(4-methoxyphenyl)-1,2,3,4,5,6-hexahydro-1,5-methano-pyrido[1,2a][1,5]diazocin-8-one;
9-(2-ethoxy-5-methylphenyl)-1,2,3,4,5,6-hexahydro-1,2-methano-pyrido[1,2a][1,5]diazocin-8-one;
9-(2-benzofuranyl)-1,2,3,4,5,6-hexahydro-1,5-methano-pyrido[1,2a][1,5]diazocin-8-one;
9-(2-thienyl)-1,2,3,4,5,6-hexahydro-1,5-methano-pyrido[1,2a][1,5]diazocin-8-one;
9-(3-thienyl)-1,2,3,4,5,6-hexahydro-1,5-methano-pyrido[1,2a][1,5]diazocin-8-one;
9-(3-(4-methylthienyl)]-1,2,3,4,5,6-hexahydro-1,5-methano-pyrido[1,2a][1,5]diazocin-8-one;
9-[2-(3-methylthienyl)]-1,2,3,4,5,6-hexahydro-1,5-methano-pyrido[1,2a][1,5]diazocin-8-one;
9-[3-(2-fluoropyridyl)]-1,2,3,4,5,6-hexahydro-1,5-methano-pyrido[1,2a][1,5]diazocin-8-one;
9-(2-pyridyl)-1,2,3,4,5,6-hexahydro-1,5-methano-pyrido[1,2a[1,5]diazoin-8-one;
9-(2-furanyl)-1,2,3,4,5,6-hexahydro-1,2-methano-pyrido[1,2a][1,5]diazocin-8-one;
9-(3-furanyl)-1,2,3,4,5,6-hexahydro-1,5-methano-pyrido[1,2a][1,5]diazocin-8-one;
9-(2-trifluoromethylphenyl)-1,2,3,4,5,6-hexahydro-1,5-methano-pyrido[1,2a][1,5]diazocin-8-one;
9-(4-trifluoromethylphenyl)-1,2,3,4,5,6-hexahydro-1,5-methano-pyrido[1,2a][1,5]diazocin-8-one;
9phenyl-1,2,3,4,5,6-hexahydro-1,5-methano-pyrido[1,2a][1,5]diazocin-8-one;
11-phenyl-1,2,3,4,5,6-hexahydro-1,5-methano-pyrido[1,5a][1,5]diazocin-8-one;
9-(2-methylphenyl)-1,2,3,4,5,6-hexahydro-1,5-methano-pyrido[1,2a][1,5]diazocin-8-one;
9-(3-acetylphenyl)-1,2,3,4,5,6-hexahydro-1,5-methano-pyrido[1,2a][1,5]diazocin-8-one;
9-(2-chlorophenyl)-1,2,3,4,5,6-hexahydro-1,5-methano-pyrido[1,2a][1,5]diazocin-8-one;
9-(3,4-dichlorophenyl)-1,2,3,4,5,6-hexahydro-1,5-methano-pyrido[1,2a][1,5]diazocin-8-one;
9-(2-fluorophenyl)-1,2,3,4,5,6-hexahydro-1,5-methano-pyrido[1,2a][1,5]diazocin-8-one;
9-(4-fluorophenyl)-1,2,3,4,5,6-hexahydro-1,5-methano-pyrido[1,2a][1,5]diazocin-8-one;
9-(3-fluorophenyl)-1,2,3,4,5,6-hexahydro-1,5-methano-pyrido[1,2a][1,5]diazocin-8-one;
9-(3,5-difluorophenyl)-1,2,3,4,5,6-hexahydro-1,5-methano-pyrido[1,2a][1,5]diazocin-8-one;
9-(2,4-difluorophenyl)-1,2,3,4,5,6-hexahydro-1,2-methano-pyrido[1,2a][1,5]diazocin-8-one;
9-(2-fluoro-4-chlorophenyl)-1,2,3,4,5,6-hexahydro-1,5-methano-pyrido[1,2a][1,5]diazocin-8-one;
9-(2-fluoro-4-methoxyphenyl)-1,2,3,4,5,6-hexahydro-1,5-methano-pyrido[1,2a][1,5]diazocin-8one;
9-(2,5-difluorophenyl)-1,2,3,4,5,6-hexahydro-1,5-methano-pyrido[1,2a][1,5]diazocin-8-one;
9-(2-thiazoyl)-1,2,3,4,5,6-hexahydro-1,5-methano-pyrido[1,2a][1,5]diazocin-8-one;

The invention also relates to compounds of the formula

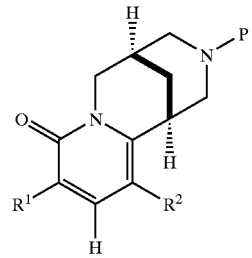

III wherein P is defined as $R^3$ or is selected from t-butoxycarbonyl (t-BOC), acetyl, benzoyl, trifluoroacetyl and carbobenzyloxy (CBZ) and $R^1$ and $R^2$ are each independently selected from H, halo, boronic acid, carboalkoxy, carboxyaldehyde, cyano, ethynyl, acyl, 2-propenyl, amino, mono and dialkylamino, aryl and heteroaryl with the proviso that $R^1$ and $R^2$ are not both hydrogen.

Preferred compounds of the formula III, as described above, are those wherein P is t-BOC, acetyl and trifluoroacetyl and each $R^1$ and $R^2$ is independently selected from hydrogen, fluoro, bromo, chloro, iodo, $(C_1-C_6)$alkyl, carboalkoxy, carboxyaldehyde, cyano, acetyl, propanoyl, 2,2-dimethylpropanoyl, 2-methylpropanoyl, butanoyl, pentanoyl, 2-propenyl, dimethylamino, with the proviso that $R^1$ and $R^2$ are not both hydrogen.

Most preferred compounds of formula III are selected from:

N-t-BOC-9-methyl-1,2,3,4,5,6-hexahydro-1,5-methano-pyrido[1,2a][1,5]diazocin-8-one;

N-t-BOC-9-iodo-1,2,3,4,5,6-hexahydro-1,5-methano-pyrido[1,2a][1,5]diazocin-8-one;

N-cBz-9-iodo-1,2,3,4,5,6-hexahydro-1,5-methano-pyrido[1,2a][1,5]diazocin-8-one;

N-trifluoroacety-9-iodo-1,2,3,4,5,6-hexahydro-1,5-methano-pyrido[1,2a][1,5]diazocin-8-one;

N-trifluoroacety-9-bromo-1,2,3,4.5,6-hexahydro-1,5-methano-pyrido[1,2a][1,5]diazocin-8-one;

N-acetyl-9-iodo-1,2,3,4,5,6-hexahydro-1,5-methano-pyrido[1,2a][1,5]diazocin-8-one;

N-t-BOC-9-boronic acid -1,2,3,4,5,6-hexahydro-1,5-methano-pyrido[1,2a][1,5]diazocin-8-one;

N-acetyl-9-bromo-1,2,3,4,5,6-hexahydro-1,5-methano-pyrido[1,2a][1,5]diazocin-8-one;

N-t-BOC-9-acetyl-1,2,3,4,5,6-hexahydro-1,5-methano-pyrido[1,2a][1,5]diazocin-8-one;

N-trifluoroacety-9-acetyl-1,2,3,4,5,6-hexahydro-1,5-methano-pyrido[1,2a][1,5]diazocin-8-one;

N-cBz-9-acetyl-1,2,3,4,5,6-hexahydro-1,5-methano-pyrido[1,2a][1,5]diazocin-8-one;

N-acetyl-9-acetyl-1,2,3,4,5,6-hexahydro-1,5-methano-pyrido[1,2a][1,5]diazocin-8-one;

N-t-BOC-9-cyano-1,2,3,4,5,6-hexahydro-1,5-methano-pyrido[1,2a][1,5]diazocin-8-one;

N-t-BOC-9-ethynyl-1,2,3,4,5,6-hexahydro-1,5-methano-pyrido[1,2a][1,5]diazocin-8-one;

N-t-BOC-9-dimethylamino-1,2,3,4,5,6-hexahydro-1,2-methano-pyrido[1,2a][1,5]diazocin-8-one;

N-t-BOC-9-(2-propenyl)-1,2,3,4,5,6-hexahydro-1,5-methano-pyrido[1,2a][1,5]diazocin-8-one;

N-t-BOC-9-(2-propyl)-1,2,3,4,5,6-hexahydro-1,5-methano-pyrido[1,2a][1,5]diazocin-8-one;

N-t-BOC-9-(2-(1,2-propanediol)-1,2,3,4,5,6-hexahydro-1,5-methano-pyrido[1,2a][1,5]diazocin-8one;

N-t-BOC-9-carbomethoxy-1,2,3,4,5,6-hexahydro-1,5-methano-pyrido[1,2a][1,5]diazocin-8-one;

N-t-BOC-9-carboxyaldehyde-1,2,3,4,5,6-hexahydro-1,5-methano-pyrido[1,2a][1,5]diazocin-8-one;

N-t-BOC-9-bromo-1,2,3,4,5,6-hexahydro-1,5-methano-pyrido[1,2-a][1,5]diazocin-8-one;

N-t-BOC-11-bromo-1,2,3,4,5,6-hexahydro-1,5-methano-pyrido[1,2-a][1,5]diazocin-8-one;

N-t-BOC-9,11-dibromo-1,2,3,4,5,6-hexahydro-1,5-methano-pyrido[1,2-a][1,5]diazocin-8-one (9,11-dibromo-t-BOC-cytisine);

N-t-BOC-9-chloro-1,2,3,4,5,6-hexahydro-1,5-methano-pyrido[1,2-a][1,5]diazocin-8-one;

N-t-BOC-11-chloro-1,2,3,4,5,6-hexahydro-1,5-methano-pyrido[1,2-a][1,5]diazocin-8-one;

N-t-BOC-9,11-dichloro-1,2,3,4,5,6-hexahydro-1,5-methano-pyrido[1,2-a][1,5]diazocin-8-one;

N-t-BOC-9-flouro-1,2,3,4,5,6-hexahydro-1,5-methano-pyrido[1,2a][1,5]diazocin-8-one;

N-t-BOC-11-flouro-1,2,3,4,5,6-hexahydro-1,5-methano-pyrido[1,2-a][1,5]diazocin-8-one; and N-t-BOC-9,11-diflouro-1,2,3,4,5,6-hexahydro-1,5-methano-pyrido[1,2-a][1,5]diazocin-8-one;

The invention also relates to compounds of the formula

II

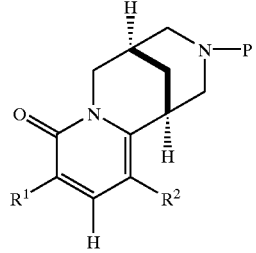

wherein $R^4$ is H, P is is selected from t-butoxycarbonyl (t-BOC), acetyl, benzoyl, trifluoroacetyl and carbobenzyloxy (CBZ), and $R^1$ and $R^2$ are each independently selected from H, $(C_1-C_6)$alkyl, $(C_1-C_6)$alkenyl and $(C_6-C_{10})$aryl, with the proviso that $R^1$ and $R^2$ are not both hydrogen.

More particularly, the invention provides compounds of formula II, as described above, wherein $R^1$ and $R^2$ are each independently selected from H, ethyl, methyl, vinyl and phenyl.

Most preferred compounds of formula II are selected from

N-t-BOC-11-vinyl-1,2,3,4,5,6-hexahydro-1,5-methano-pyrido[1,2-a][1,5]diazocin-8one (11-vinyl-t-BOC-cytisine);

N-t-BOC-11ethyl-1,2,3,4,5,6-hexahydro-1,5-methano-pyrido[1,2-a][1,5]diazocin-8-one (11-ethyl-t-BOC-cytisine); and N-t-BOC-11-phenyl-1,2,3,4,5,6-hexahydro-1,5-methano-pyrido[1,2a][1,5]diazocin-8-one (11-phenyl-t-BOC-cytisine).

Unless otherwise indicated, the term "halo", as used herein includes fluoro, chloro, bromo and iodo.

Unless otherwise indicated, the term "alkyl", as used herein, may be straight, branched or cyclic, and may include straight and cyclic moieties as well as branched and cyclic moieties.

Unless otherwise indicated, the term "one or more substituents", as used herein, refers to from one to the maximum number of substituents possible based on the number of available bonding sites.

The term "one or more carbons of said non-aromatic ring", as used herein, refers to from one to all of the carbon atoms that are part of the non-aromatic ring of any of the, aryl-fused or heteroaryl-fused systems described above, and not part of the aromatic ring of said aryl-fused system.

The term "one or more carbons of said aromatic ring", as used herein, refers to from one to all of the carbon atoms that are part of the aromatic ring of any of the aryl-fused and heteroaryl-fused systems described above.

The compounds of formula I have optical centers and therefore may occur in different enantiomeric configurations. The invention includes all enantiomers, diastereomers, and other stereoisomers of such compounds of formula I, as well as mixtures thereof.

The present invention also relates to all radiolabelled forms of the compounds of the formulae I. Preferred radiolabelled compounds of formula I are those wherein the radiolabels are selected from as $^3H$, $^{11}C$, $^{14}C$, $^{18}F$, $^{123}I$ and $^{125}I$. Such radiolabelled compounds are useful as research and diagnostic tools in metabolism pharmacokinetics studies and in binding assays in both animals and man.

The present invention also relates to a pharmaceutical composition for use in reducing nicotine addiction or to aid in the cessation or lessening of tobacco use in a mammal comprising an amount of a compound of the formula I, or a pharmaceutically acceptable salt or prodrug thereof, effective in reducing nicotine addiction or to aid in the cessation or lessening of tobacco use and a pharmaceutically acceptable carrier.

The present invention also relates to a method for reducing nicotine addiction in a mammal, comprising administering to a mammal an amount of a compound of the formula I, or a pharmaceutically acceptable salt or prodrug thereof, effective in reducing nicotine addiction or lessing of tobacco use.

Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleate, di-p-toluoyl tartaric acid, and mandelic acid.

DETAILED DESCRIPTION OF THE INVENTION.

Except where otherwise stated, R, $R^1$, $R^2$ and $R^3$, and formulae I, II, III, IV and V, in the reaction schemes and discussion that follow are defined as above

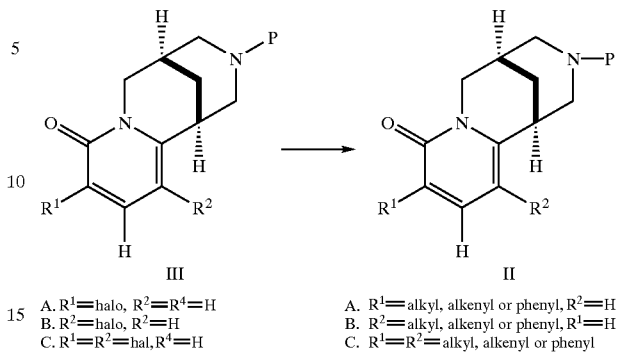

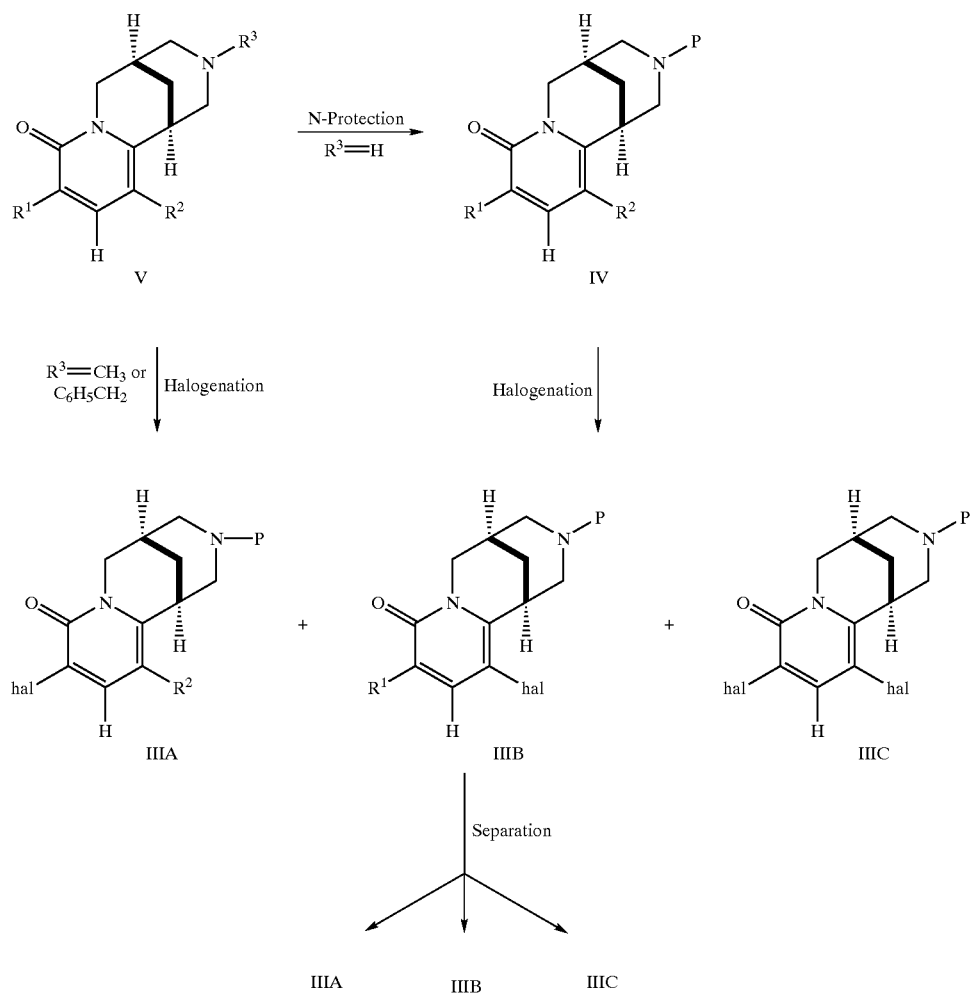

-continued
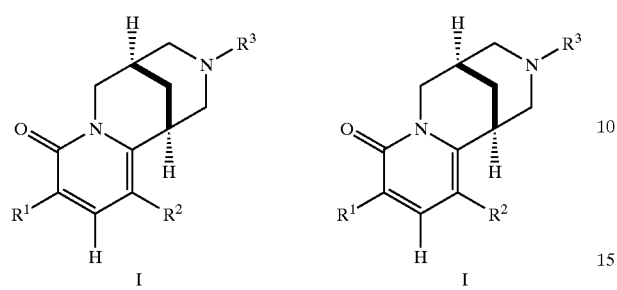
A. R¹=halo, R²=R³=H
B. R²=halo, R¹=R³=H
C. R¹=R²=halo, R³=H
A. R¹=alkyl, alkenyl or phenyl, R²=R³=H
B. R²=alkyl, alkenyl or phenyl, R¹=R³=H
C. R¹=R²=alkyl, alkenyl or phenyl, R³=H
SCHEME 3
V or I (R³=H)
↓ Alkylation
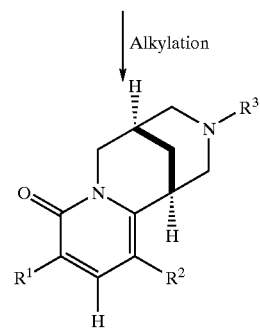
(R³=benzyl or methyl and R¹ and R² are as defined above for V or I)
SCHEME 4
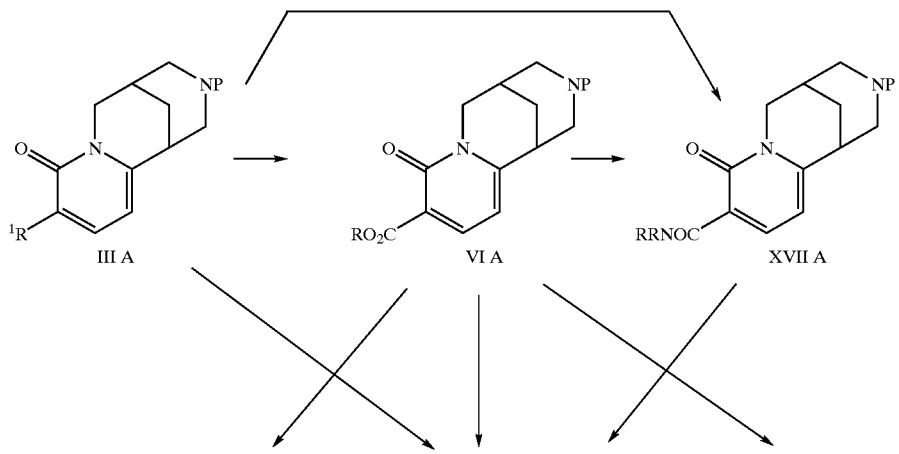
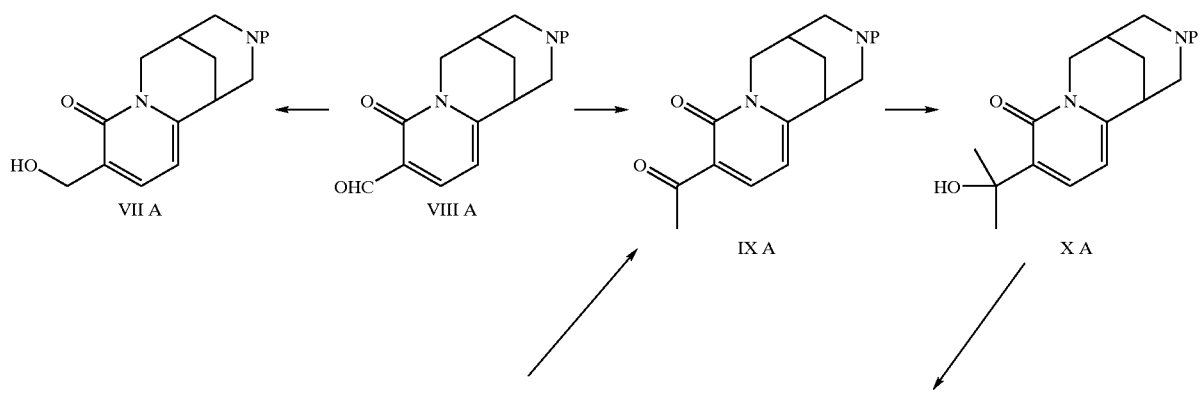

-continued

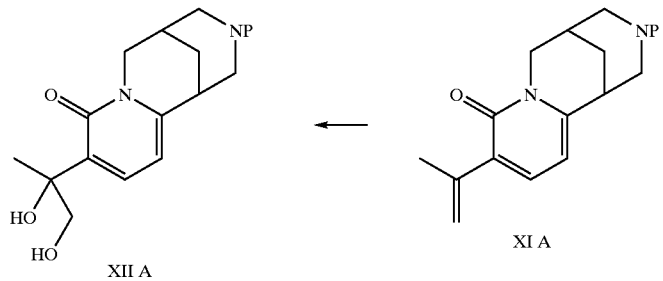

SCHEME 5

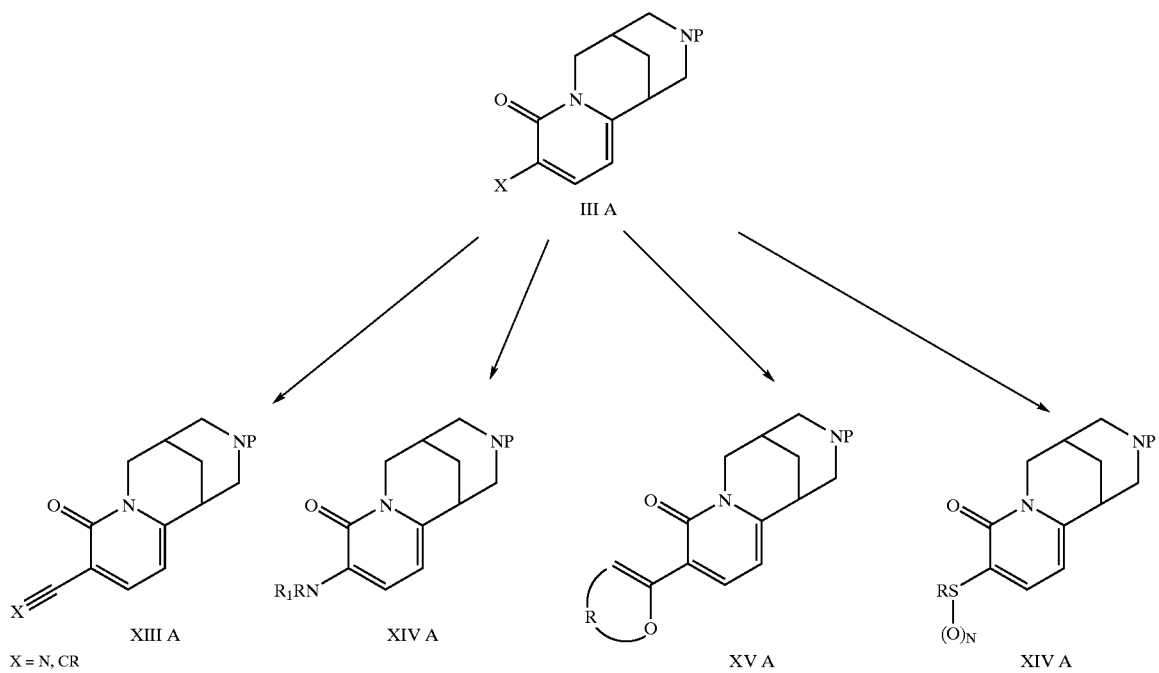

In each of the reactions discussed below, or illustrated in Schemes 1–3, above, pressure is not critical unless otherwise indicated. Pressures from about 0.5 atmospheres to about 5 atmospheres are generally acceptable, with ambient pressure, i.e., about 1 atmosphere being preferred as a matter of convenience.

Referring to Scheme 1, compound V (cytisine, when $R^1$, $R^2$ and $R^3$ are all hydrogen) is protected to form the compound of the formula IV wherein P is an appropriate nitrogen protecting group, as known in the art, including t-BOC, CBZ, methyl, benzyl, trifluoroacetyl, acetyl and benzoyl. If desired, the N-protection step may be eliminated Compound IV (or V wherein $R^3$ is methyl or benzyl) is halogenated to form a mixture of halogenated products of the formula III wherein one or both of $R^1$ and $R^2$ is a halogen atom, depending upon the conditions and the reaction stoichiometry, preferably iodo, bromo or chloro. Thus, when using one molar equivalent of a suitable halogenating agent, products IIIA and IIIB predominate. However, when two molar equivalents of halogenating agent are used compound IIIC predominates. The nitrogen can be protected by acetyl and trifluoroacetyl, t-BOC, CBZ, benzyl, methyl or any of the readily removable N-protecting groups known in the art. Alternatively, no protecting group need be used.

The t-BOC group can be introduced using a reagent such as di-t-butyldicarbonate, di-t-butylpyrocarbonate, 2-(t-butoxycarbonyloxyimino)-2-phenylacetonitrile (t-BOC-ON), t-BOC-azide, t-BOC-chloride, t-BOC-fluoride and 2-(t-butoxycarbonyloxy)phthalimide or similar reagents wherein t-BOC refers to the residue tertiary butoxycarbonyl a useful protecting group. The reaction is conducted in a suitable solvent or mixture of solvents, including, but not limited to the following methylene chloride, ethyl acetate, chloroform, benzene, toluene, ether, tetrahydrofuran (THF), dichloroethane and water with a suitable base including, but not limited to, the following: sodium, lithium and potassium carbonates, bicarbonates and hydroxides, imidazole, dimethylaminopyridine and trialkylamines such as triethylamine. The reaction requires 0.5 to 24 hours for completion. The temperature is not critical, the reaction being run between room temperature and the reflux temperature of the solvent or mixture of solvents. The reaction is generally run at a pressure between 0.5 and 2.0 atmospheres, preferably at atmospheric pressure. It is preferably carried out at reflux for 1–2 hours with t-BOC dicarbonate in a mixture of methylene chloride and water with sodium bicarbonate as base. If the protecting group is CBZ (carbobenzyloxy) it can be incorporated by the general procedure described above beginning with the compound of the formula V and carbobenzyloxy chloride (CBZ—Cl) instead of the t-BOC source.

Referring to Scheme 3, the N-methyl or N-benzyl group can be introduced by nitrogen alkylation of cytisine or the compound of the formula I (or V when $R^3$ is hydrogen) with a suitable reagent. Suitable reagents for N-benzylation include benzyl halides, such as the bromide, chloride and iodide and sulfonic acid esters such as the mesylate, tosylate and triflate in an inert solvent such as dimethylformamide (DMF), N-methylpyrrolidone, dimethylsulfoxide (DMSO), acetone, ethanol, methanol, acetonitrile, THF and water and mixtures thereof with a base such as sodium or potassium hydride, 1,8-diazobicyclo[5 4 0]undec-7-ene (DBU), potassium t-butoxide, tri($C_1$–$C_6$)alkylamines such as triethylamine, sodium, lithium and potassium carbonates, bicarbonates and hydroxides, imidazole and dimethylaminopyridine. Aprotic solvents must be used when the bases, such as the hydrides, are reactive to protic solvents such as water The reaction can be run at temperatures between 0° C. and the reflux temperature of the solvent for a period of 0.5 hours to 48 hours. It is preferably carried out with benzyl chloride in acetone at reflux for 1–2 hours using potassium carbonate as base at atmospheric pressure.

For N-methylation, suitable reagents are methyl iodide or bromide, dimethylsulfate and methyl triflate using the conditions described above for N-benzylation. The reaction is preferably carried out with methyl iodide in acetone at reflux for 1–2 hours using potassium carbonate as base.

Alternatively, N-benzylation may be carried out in the following manner. The compound of formula I (or V wherein $R^3$ is hydrogen), in an inert solvent, such as ($C_1$–$C_6$)alkanols, preferably methanol or ethanol, and halocarbons such as methylene chloride, chloroform and dichloroethane and acetic acid and water and mixtures thereof, is treated with benzaldehyde and a reducing agent such as sodium triacetoxyborohydride, tetraalkylammonium triacetoxyborohydride, sodium cyanoborohydride, sodium borohydride or similar reagents with or without a catalytic amount of an acid, such as acetic acid or trifluoroacetic acid at a temperature between 0° C. and the reflux temperature of the solvent, or mixture of solvents, for a period of 0.5 to 48 hours at atmospheric pressure. The reaction is preferably carried out in dichloroethane at room temperature with benzaldehyde, sodium triacetoxyborohydride and a catalytic amount of acetic acid for a period of two hours.

N-Methylation can, alternatively, be carried out with a source of formaldehyde such as formaldehyde gas, formalin, paraformaldehyde or trioxane and a suitable reducing agent, as described above, in an inert solvent, as described above or, alternatively, in a solvent such as refluxing formic acid without a separate reducing agent. When the source of formaldehyde is trioxane the reaction must be effected in the presence of an acid such as the the formic acid, above. N-Methylation can also be carried out in an inert solvent such as methanol, ethanol or water in the presence of a source of formaldehyde and a palladium catalyst, such as palladium on carbon, under 1–10 atm. of hydrogen gas for a period of 1–24 hours.

Acylation of the secondary nitrogen with either acetyl chloride, acetic anhydride or trifluoroacetic anhydride may be carried out in a suitable inert solvent or mixture of solvents such as methylene chloride, dichloroethane, acetonitrile, toluene, benzene, ethyl acetate, chloroform, ether water or THF. Usually an equivalent of base or an excess of base is used. Bases such as pyridine, triethyl amine, diisopropylethylamine, sodium or potassium carbonate or bicarbonate, hydroxides, imidazole, or dimethylaminopyridine may be used interchangeably. In some or all cases, the base may be used as the solvent as in the case of pyridine or aqueous carbonate solutions. The temperature is not critical but is generally held between −20° C. and ambient. The reaction requires 0.5 to 24 hours for completion Most preferably, the acylating agent is acetic anhydride or trifluoroacetic anhydride in a solvent such as dichloromethane with a base such, as pyridine at 0° C. to room temperature for 1 hour.

Referring to Scheme 1 bromination of compound IV (or V when $R^3$ is methyl or benzyl) is carried out in an inert solvent such as methylene chloride, ethyl acetate, chloroform, benzene, toluene, tetrahydrofuran (THF) with a brominating reagent such as bromine, N-bromosuccinimide (NBS), 1,3-dibromo-5,5-dimethylhydantoin, N-bromoacetamide or similar reagents. The reaction can be carried out at atmospheric pressure with or without a suitable inert base such as sodium, lithium or potassium bicarbonate and tri($C_1$–$C_6$)alkylamines such as triethylamine at temperatures between ambient and the reflux temperature of the solvent at atmospheric pressure for a period of 0.5 to 24 hours. It is preferably carried out with NBS in methylene chloride at reflux for 1.5 hours.

Chlorination of compound IV is effected, under the conditions described above for the bromination reactions including use of the same solvents and water, by treatment with a chlorinating reagent such as chlorine, N-chlorosuccinimide (NCS) and N-chloroacetamide or a similar reagent at temperatures between 0° C. and the reflux temperature of the solvent at atmospheric pressure for a period of 0.5 to 24 hours. It is preferably carried out with NCS in methylene chloride at reflux for 1–2 hours or chlorine in water at 0° C. for 1–2 hours.

Iodination of compound IV is effected under the conditions described above for chlorination or bromination. This includes the use of the same solvents and water by treatment with an iodinating agent such as N-iodosuccinimide, iodine or ICl or a similar reagent. The iodination is conducted at a temperature between 0° C. and the reflux point of the solvent while at atmospheric pressure for a period of 0.5–24 hours. Alternatively it is carried out in methanol or methanol-methylene chloride with a suitable carbonate base such as sodium, potassium, magnesium or calcium carbonates. It is preferably carried out in methanol-methylene chloride with ICl and a base such as calcium carbonate.

The halogenation reactions generally produce a mixture of mono and dihalogenated products depending upon the exact conditions of time, temperature and reagents. These may be varied to favor a particular substitution pattern as detailed in the experimental section. The mixture can be purified to a single product by crystallization or trituration from a solvent or mixture of solvents such as diethyl ether, isopropylether and ethyl acetate-hexanes. Alternatively, the mixture may be separated -by chromatography on silica gel or another support eluting with a mixture of methylene chloride or chloroform or ethyl acetate with methanol or similarly with mixtures of ethyl acetate with hexanes. It is preferably separated through crystallization from diethyl ether or mixtures of diethyl ether and another solvent such as hexane or by chromatography on silica gel eluting with a mixture of methylene chloride and methanol.

Scheme 2 illustrates the further transformation compound III, as exemplified by compound IIIA, wherein $R^2$ is hydrogen and $R^1$ is bromo or iodo, to the compound of the formula IIA (Although the following procedures are discussed with respect to the compounds of the formulae IIIA, IIA, and IA they are equally applicable to the B and C counterparts thereof). Thus, replacement of the bromo or iodo atom by optionally substituted $(C_1-C_6)$alkyl or $(C_1-C_6)$alkenyl or $(C_6-C_{10})$aryl may be carried out by reaction of the bromide or iodo or dibromide with an organometallic compound such as tetra$(C_1-C_6)$ alkyltin, $(C_1-C_6)$alkenyltri-$(C_1-C_6)$alkyltin or phenyltri$(C_1-C_6)$alkyltin under the influence of a palladium catalyst such as tetrakis(triphenylphosphine) palladium, transbenzylchlorobis (triphenylphosphine) palladium, palladium on carbon, palladium acetate, palladium chloride, palladium trifluoroacetate, palladium trisdibenzylideneacetone, bis (triphenylphoshine)palladium dichloride or other sources of coordinated palladium (0) or palladium (II). The reaction can be carried out in a solvent such as hexamethylphosphoramide (HMPA), N-methylpyrrolidone, ethanol, methanol, water or DMF at temperatures from ambient to 130° C. for 6–48 hours at 1–2 atmospheres pressure. Alternatively, the organometallic reagent can be a $(C_1-C_6)$alkyl, $(C_1-C_6)$alkenyl or arylzinc halide wherein halide refers to chloride, bromide and iodide. The organometallic reagent can also be a $(C_1-C_6)$ alkyl ester of a $(C_1-C_6)$alkyl, $(C_1-C_6)$alkenyl, $(C_6-C_{10})$aryl or $(C_6-C_{10})$heteroaryl boronic acid. The most preferred conditions involve reaction of the bromide or dibromide with an organotin compound such as tetramethyltin, vinyl(trimethyl) tin, vinyl(tri-n-butyl)tin, phenyl(trimethyl)tin and phenyl (tri-n-butyl)tin in the presence of trans-benzylchlorobis (triphenylphosphine)palladium in HMPA at 40 to 80.0° C. for 20 to 40 hours. Other preferred conditions for forming the the compound (group) of the formula II is by treatment of the compound of formula III with the aryl, alkenyl or heteroaryl boronic acid, in a mixture of ethanol and water, in the presence of tetrakis(triphenyl)phosphinepalladium (0) and a suitable base such as sodium, potassium or lithium carbonate or bicarbonate with sodium carbonate generally preferred.

Scheme 4 illustrates the further transformation of compound III as exemplified by compound III A, wherein R2, R4=H and R1 is bromo or iodo, to the compound of formula VI. (Although the following procedures are discussed with respect to the compounds of formulae IIIA, and VI A they are equally applicable to the B and C counter parts thereof.) Thus, replacement of the bromo or iodo atom with carboalkoxy or carboxy may be carried out by the reaction of the bromide or the iodo in an alcoholic solvent such as methanol, ethanol, isopropanol, tert-butanol etc. or alternatively in water with or without a suitable co-solvent such as DMSO or DMF under 1–200 atmospheres of carbon monoxide gas in the presence of catalytic palladium metal with or without a ligand. Sources of palladium such as palladium on carbon, palladium acetate, palladium chloride, palladium trifluoroacetate, palladium tris(dibenzylideneacetone), palladium bis(dibenzylideneacetone) or other sources of ligated palladium (0) such as tetrakis(triphenylphosphine)palladium or palladium (II) salts such as DIS triphenylphoshinepalladium dichloride are effective in this transformation Suitable ligands for this transformation are, 1,3-diphenylphosphinylpropane (dppp), 1,3-diphenylphosphinylethane (dppe) 1,3-diphenylphosphinylbutane (dppb), triphenylphosphine, 2,2'-bis(diphenyl phosphino)-1,1-binaphthyl (BINAP), 1,1'-bis(diphenylphosphino) ferrocene (dppf) or other commercially available bidentate ligands are satisfactory in this transformation. The reaction was conducted in the presence of a suitable base such as sodium, lithium or potassium carbonate, sodium, lithium or potassium bicarbonate or sodium, lithium or potassium hydroxides Temperature of the reaction can vary from room temperature to 100° C. for a time of between 1 and 24 hours. Most preferably the reaction is carried out between iodide or bromide IIIA in methanol with palladium acetate and dppp under 16 psi carbon monoxide and potassium bicarbonate for a period of 16 hrs at 70° C.

A similar process, as described above for the formation of the ester may be used to produce the carboxamide of the formula XVIIA from a compound of the formula IIIA ($R^1$=I or Br). Thus, replacement of the bromo or iodo atom with a substituted or unsubstituted carboxamide may be carried out by the reaction of the bromide or the iodo under 1–200 atmospheres of carbon monoxide gas in the presence of catalytic palladium metal with or without a ligand using a source of palladium as detailed above. Typically the amine is used as the solvent or if it is a gas then it is used as a staurated solution in an inert solvent. Preferred conditions, using an amine such as benzyl amine as solvent under 50 psi carbon monoxide at 50° C. in the presence of catalytic bis-triphenylphosphine palladium (II) chloride for 24 hours. Alternatively, the amide XVIIA may be prepared from VIA under standard conditions of ammonolysis or aminolysis with or without a catalyst Thus a saturated solution of a suitable amine gas in an inert solvent or, if it is a liquid, the neat amine is heated at atmospheric pressure or at an elevated pressure of from 1–5 atmospheres to produce the amide directly. Alternatively, the reaction may be run under mild conditions using a catalyst such as trialkylaluminum or trialkylstannanes.

The ester or carboxylate VI as well as the carboxamide XVIIA may optionally be further transformed to compounds VII, VIII, IX and X by hydride reduction or by addition of a organometallic nucleophile. In the case of VII, at least two equivalents of hydride is needed to reduce VI whereas the formation of VIII only requires the addition of one hydride equivalent. Similarly, In the case of X, addition of at least two equivalents of organometallic are needed to afford X whereas addition of a single equivalent will afford IX. Proper control of experimental conditions can afford mono or bis addition of VI and specific conditions for each transformation are known in the art (for reviews see: O'Neill B. T. in Comprehensive Organic Synthesis; B. M. Trost Editor, Vol 1, 397–458, Pergamon, 1991 or Reductions in Organic Chemistry, 2nd Ed, Hudlicky, M., ACS Washington D.C. 1996). Suitable reducing agents for the process VI to VIII and VII are lithium aluminum hydride, sodium, potassium or lithium borohydride, lithium triethylborohydride, diisobutyl aluminum hydride (DiBAL-H), aluminum hydride, amino-borane lithium salt and similar reagents Generally, these reactions may be conducted in solvents such as THF or diethyl ether, t-butylmethyl ether, diisopropyl ether, toluene, dichloromethane, dichloroethane or dimethoxyethane. The temperature of the reaction may vary but can be run between −78° C. and ambient temperature or between ambient temperature and the reflux point of the solvent. The reaction generally requires between 0.5 and 24 hours for completion and generally is run at ambient pressure. Most preferred conditions are DIBAL-H in methylene chloride at −78° C. for 3 hours.

Suitable organometallic reagents for the process of VI to IX and X as well as XVII to IX include (C1–C6)alkyl lithiums, (C1–C6)alkyl magnesium halides (wherein halide refers optionally to chloride, bromide or iodide), or (C1–C6) alkyl cuprate or di(C1–C6)alkyl cuprates. More specifically methyl lithium, methyl magnesium halide, t-butyl lithium, t-butyl magnesium halide, isopropyl lithium, isopropyl magnesium halide, n-butyl lithium, n-butyl magnesium halide, s-butyl lithium, s-butyl magnesium halide. Most specifically methyl lithium and methyl magnesium halide. The reaction can be run in several inert solvents such as THF or diethyl ether, dimethoxyethane or similar solvents. The temperature of the reaction may vary but can be run between −78° C. and ambient temperature or between ambient temperature and the reflux point of the solvent. The reaction generally requires between 0.5 and 24 hours for completion and generally is run at ambient pressure. The compound of formula X may also be transformed into compounds of this invention by modification of the tertiary alcohol. For example, the compound of formula IX may be obtained through the sequence X to XI to XII followed by conversion directly to IX. This sequence may be completed with or without isolation of the individual intermediates which are themselves a part of the subject matter of this case. Transformation of X to XI may be carried out under acidic conditions or alternatively by first transforming the tertiary alcohol to a suitable leaving group such as a halogen or a group such as a mesylate, triflate, tosylate or other suitable activating group followed by base catalyzed elimination. The reaction under acidic conditions may use one of the following acidic reagents in water with or without a co-solvent acetic, trifluoroacetic, sulfuric, hydrochloric, hydrobromic acid and other similar reagents or alternatively silica gel may be used. Suitable solvents include water, methanol, ethanol, isopropanol, THF or diethyl ether, t-butylmethyl ether, diisopropyl ether, toluene, dichloromethane, dichloroethane chloroform or dimethoxyethane, ethyl acetate acetonitrile or similar solvents or combination of solvents. The transformation from X to XI may be completed at a temperature of 0° C. to room temperature for a period of 5 minutes to 5 hours. The most preferred conditions are trifluoroacetic acid in methylene chloride at 0° C. to room temperature for a period of two hours.

Conversion of XI to IX may be carried out with or without isolation of the intermediate XII Formation of XII can be accomplished with a reagent such as osmium tetroxide or potassium permanganate in a suitable solvent or combination of solvents such as water, acetone t-butanol dioxane or THF. The osmium tetroxide can be used in catalytic quantities if combined with a second oxidant such as N-methylmorpholine-N-oxide or trimethyl amine N-oxide, triethylamine-N-oxide or sodium periodate. Generally the reaction is carried out at room temperature but may be run between 0° C. and the reflux point of the solvent for a period of 12 to 48 hours The most preferred conditions involve the use of catalytic osmium tetroxide with N-methylmorpholine-N-oxide and sodium periodate in dioxane/water at room temperature for 24 hours to afford IX directly. Alternatively, XI may be directly converted to IX with ozone gas under standard conditions. Thus ozone in oxygen may be introduced to a solution of XI in a suitable solvent such as methanol, ethanol, isopropanol, toluene, dichloromethane, dichloroethane chloroform, ethyl acetate and acetonitrile or similar solvents or combination of solvents. The reaction is generally run at −78° C. but may also be run between −78° C. to ambient temperature for a period of 5 minutes to 1 hour. An indicator such as sudan red may or may not be employed to indicate when the reaction is complete. The reaction is then quenched under reducing conditions to afford the product IX. Suitable reducing agents include but are not limited to dimethyl sulfide, zinc and acetic acid, hydrogen/palladium on carbon, triphenyl phosphine or similar reagents. The most preferred conditions are ozone in methylene chloride at −78° C. in the presence of sudan red indicator followed by addition of dimethyl sulfide.

Direct conversion of III A ($R_1$=Br or I) to IX may also be accomplished through halogen metal exchange and acylation. Thus the bromide or iodide IIIA may be treated with a metal such as lithium, sodium, magnesium or zinc to form the corresponding organometallic which is then quenched with a suitable acylating agent. Suitable acylating agents include esters, thioesters, acids, amides, N-methoxy-N-methylamides, anhydrides, acid chlorides and similar agents. The reaction may be initiated by using the metal directly or by prior formation of a metal complex with an aromatic agent such as napthalene or biphenyl such as lithium naphthalide or through the use of an organometallic such as n-butyl lithium, t-butyl lithium, s-butyl lithium, methyl magnesium halide or similar reagents. Suitable solvents for this transformation include THF, ether, dimethoxyethane as well as similar reagents. The most preferred conditions are n-butyl lithium. In THF at −78° C. to 0° C. using N-methoxy-N-methylamides for 2.5 hours.

Direct conversion of VIIIA to IX A may be accomplished as described above for the conversion of VIA to IX A, however, a second step is required to convert the intermediate secondary alcohol (not shown) in to the ketone. Suitable reagents for this transformation include chromium trioxide and chromium trioxide pyridine complex, pyridium chlorochromate, pyridium dichromate, potassium permanganate, hypochlorous acid, mixtures of DMSO with oxalyl chloride or trifluoracetic anhydride and other well known reagents capable of oxidation of alcohols to ketones.

Scheme 5 illustrates the further transformation of compound III as exemplified by compound III A, wherein R2, R4=H and R1 is bromo or iodo, to the compounds of formula XIII, XIV, XV, XVI. (Although the following procedures are discussed with respect to the compounds of formulae IIIA, and XIII A, XIV A, XV A, XVI A they are equally applicable to the B and C counter parts thereof). Thus, replacement of the bromo or iodo atom with zinc cyanide afforded XIII (X=N) under palladium catalysis in a polar aprotic solvent such as DMF, DMSO, N,N-dimethylacetamide, N-methyl pyrrolidone or similar solvents at a temperature between ambient temperature and 150° C. for a period of 6 to 48 hours at atmospheric pressure. Suitable catalysis include but are not limited to palladium tris(dibenzylideneacetone), palladium bis(dibenzylideneacetone) or other sources of ligated palladium (0) such as tetrakis(triphenylphosphine)palladium or palladium (II) salts such as bistriphenylphoshinepalladium dichloride:, 1,3-diphenyl phosphinylpropane palladium(0) [(dppp)Pd(0)], 1,3-diphenylphosphinyl ethane palladium(0) [(dppe)Pd(0)], 1,3-diphenylphosphinylbutanepalladium(0) [(dppb) Pd(0)], 2,2'-bis(diphenylphosphino)-1,1'-binaphthyl palladium(0) [(BINAP) Pd(0)], 1,1'-bis(diphenylphosphino) ferrocene palladium(0) [(dppf) Pd(0)] or other commercially available palladium sources are satisfactory in this transformation. The most preferred conditions use bromo or iodo IIIA together with zinc cyanide in DMF and tetrakis (triphenylphosphine)palladium (0) at 80° C. for 16 hours.

Alternatively, in a similar manner to that described above, one may replace the bromo or iodo atom with an acetylene to afford XIII (X=CR, wherein R=H, ($C_1$–$C_6$) alkyl, aryl including substituted alkyl, aryl). Thus treatment as above but with the substitution of an acetylene (such as trimethylsilylacetylene or other acetylenes) for zinc cyanide will lead to the formation of XIII (X=CR). Typically the reaction is run in a solvent such as diethylamine or pyrrolidine or other secondary amines with a catalyst such as copper (I)

iodide, bromide or chloride and in the presence of a palladium catalyst as described above. The reaction is run at a temperature between ambient temperature and the reflux point of the solvent for a period of 1 to 24 hours at atmospheric pressure. Typically it is run at ambient temperature for 4 hours.

Substitution of the bromo or iodo atom in III A with a primary or secondary amine R,R'NH, wherein R and R' may be any of H, ($C_1$–$C_6$) alkyl, aryl and benzyl, to afford XIV. Typically, the reaction is conducted in a solvent such as toluene, benzene, xylene, dioxane or THF at a temperature between ambient temperature and the reflux point of the solvent. Typically the reaction is conducted in toluene at about 80° C. The reaction is catalyzed with palladium metal in the presence of a suitable ligand. Sources of palladium include but are not limited to palladium acetate, palladium tris(dibenzylideneacetone), palladium bis(dibenzylideneacetone), in the presence of a ligand such as dppp, dppe, dppb, dppf, BINAP, tri-o-tolylphosphine or alternatively tetrakis(triphenylphosphine)palladium, 1,3-diphenylphosphinyl propanepalladium (0) [(dppp)Pd(0)], 1,3-diphenylphosphinyl ethane palladium(0) [(dppe)Pd(0)], 1,3-diphenylphosphinylbutane palladium(0) [(dppb)Pd(0)], 2,2'-bis(diphenylphosphino)-1,1'-binaphthyl palladium(0) [(BINAP) Pd(0)], 1,1'-bis(diphenylphosphino) ferrocene palladium(0) [(dppf) Pd(0)] or other commercially available palladium sources are satisfactory in this transformation. Most preferably 2,2'-bis(diphenylphosphino)-1,1'-binaphthyl palladium(0) [(BINAP) Pd(0)] is used. Typically a base such as sodium, potassium or lithium butoxide or sodium, potassium tert-amyloxide is used in the process. Most preferably sodium t-butoxide is used.

Substitution of the bromo or iodo atom in III A with a sulfide RSH, wherein R may be any of H, ($C_1$–$C_6$) alkyl, aryl and benzyl, to afford XVI (wherein n=0,1,2). Typically, the reaction is conducted in a solvent such as toluene, benzene, xylene, dioxane or THF at a temperature between ambient temperature and the reflux point of the solvent. Typically the reaction is conducted in toluene at about 80° C. The reaction is catalyzed with palladium metal in the presence of a suitable ligand. Sources of palladium include but are not limited to palladium acetate, palladium tris (dibenzylideneacetone), palladium bis(dibenzylideneacetone), in the presence of a ligand such as triphenylphosphine, dppp, dppe, dppb, dppf, BINAP, tri-o-tolylphosphine or alternatively tetrakis(triphenylphosphine) palladium, 1,3-diphenylphosphinyl propanepalladium (0) [(dppp)Pd(0)], 1,3-diphenylphosphinyl ethane palladium(0) [(dppe)Pd(0)], 1,3-diphenylphosphinylbutane palladium(0) [(dppb)Pd(0)]. 2,2'-bis(diphenylphosphino)-1,1'-binaphthyl palladium(0) [(BINAP) Pd(0)], 1,1'-bis(diphenylphosphino) ferrocene palladium(0) [(dppf) Pd(0)] or other commercially available palladium sources are satisfactory in this transformation. Most preferably 1,3-diphenylphosphinyl ethane palladium(0) [(dppe)Pd(0)], is used. Oxidation of the newly formed sulfide (wherein n=0) to afford the sulfoxide (wherein n=1) or the sulfone (wherein n=2), may be accomplished under standard conditions for oxidation known in the art. Typically, oxidants such as oxygen, hydrogen peroxide, OXONE, m-chloroperbenzoic acid or other per-acids such as peracetic acid and hypochlorous acid may be used.

Alternatively, substitution of the bromo or iodo atom in III A may be conducted with an alkene or a suitable vinyl ether to form XV A. The olefin or vinyl ether may be part of a ring system or alternatively, it may be part of an acyclic system. Thus R in XV may be simply ($C_1$–$C_6$) alkyl or benzyl or alternatively it may be part of a ring which includes the olefin. The ring size typically contains 5,6,7 or 8 atoms. The reaction is conducted in a suitable polar aprotic solvent such as DMF, DMSO, N,N-dimethylacetamide, N-methyl pyrrolidone or similar solvents at a temperature between ambient temperature and 150° C. for a period of 0.5 to 24 hours at atmospheric pressure. Typically the reaction is conducted in DMF at about 90° C. The reaction is catalyzed by palladium typically in the form of palladium acetate or palladium dichloride with or without a ligand such as triphenylphosphine, dppp, dppe, dppb, dppf, BINAP, tri-o-tolylphosphine. The reaction may also be run in the presence or absence of a suitable base such as sodium, lithium or potassium acetate, triethyl amine or diisopropylethylamine and alternatively in the presence or absence of teraalkyl ammonium salts such as terabutylammonium chloride, bromide, acetate or iodide. Typically the reaction is conducted between IIIA and dihydrofuran in DMF at about 90° C. with palladium acetate, triphenyl phosphine, tera-butyl ammonium acetate, potassium acetate for 16 hours. Also the reaction between III A and butyl vinyl ether is conducted in DMF at 90° C. for 1.5 hours using palladium acetate, dppf and triethyl amine The resulting product retains the olefin carbon bond which may undergo further reaction under standard conditions known in the art. These include but are not limited to hydrogenation and also reaction with aqueous acid.

The t-BOC protecting group can be readily removed from the protected products IIIA, IIA, VIA, VIIA, VIIIA, IXA, XA, XIA, XIIA, XVIIA, XVIIIA, XIVA, XVA, and XVIA described above, to form the compound IA (Scheme 2) wherein $R^3$ is hydrogen and $R^1$ is as defined previously respectively, by treatment with an acid such as hydrochloric, sulfuric, trifluoroacetic, acetic, nitric, hydrofluoric, hydrobromic and hydroiodic using water as a solvent or co-solvent or in anhydrous organic solvents such as methanol, ethanol, ether, ethyl acetate, methylene chloride and chloroform or mixtures thereof. The product is obtained as its acid salt which may be then treated with a suitable base including, but not limited to, the following: sodium, lithium and potassium carbonates, bicarbonates and hydroxides, generally, in water to afford the desired material as the free base form.

The benzyl and CBZ protecting groups can be removed from the compounds of formulae IIIA, IIA, VIA, VIIA, VIIIA, IXA, XA, XIA, XIIA, XVIIA, XIIIA, XIVA, XVA and XVIA by treatment, in a solvent such as methanol, water, acetic acid and ethyl acetate, with 1 to 10 atmospheres of hydrogen gas in the presence of a catalyst such as palladium on carbon, palladium hydroxide and palladium hydrochloride, at a temperature from ambient to about 50° C.

Compound IA, wherein $R^3$ is hydrogen, can be treated, as described above for N protection, by benzylation or methylation, to form compound IA wherein $R^3$ is benzyl or methyl.

Alternatively, if $R^3$, in compound IA, is to be benzyl or methyl and the protecting group P is benzyl or methyl no deprotection step is needed as compound IA corresponds to compound IIIA, IIA VIA, VIIA, VIIIA, IXA, XA, XIA, XIIA, XVIIA, XIIIA, XIVA, XVA and XVIA. If P is an acyl group such as a trifluoroacetyl group then it may be removed by treatment with dilute acid or base to afford a compound of the formula I. Thus treatment with aqueous sodium bicarbonate, carbonate or hydroxide and a co-solvent such as methanol, ethanol, THF, dioxane or similar inert solvents may be used. Also methanol and sodium methoxide may be used. Alternatively, aqueous acid such as dilute hydrochloric acid may be used in combination with an inert co-solvent as described above. The temperature of the reaction may range from 0° C. to the reflux point of the solvent.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are most desirably administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.02 mg to about 10 mg per kg of body weight per day is most desirably employed Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar] as well as high molecular weight polyethylene glycols. When aqueous suspensions and/or elixirs are desired for oral administration the active ingredient may be combined with various sweetening or flavoring agents, coloring matter and, if so desired, combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

Biological Assay

The effectiveness of the active compounds in suppressing nicotine binding to specific receptor sites is determined by the following procedure which is a modification of the methods of Lippiello, P. M. and Femandes, K. G. (in *The Binding of L-[$^3$H]Nicotine To A Single Class of High-Affinity Sites in Rat Brain Membranes, Molecular Pharm.*, 29, 448–454, (1986)) and Anderson, D. J. and Arneric, S. P. (in *Nicotinic Receptor Binding of $^3$H-Cystisine, $^3$H-Nicotine and $^3$H-Methylcarmbamylcholine In Rat Brain, European J. Pharm.*, 253, 261–67 (1994)).

Procedure

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (*Molec. Pharmacol.* 29, 448–454, (1986) with some modifications. Whole brains were removed, rinsed with ice-cold buffer, and homogenized at 0° in 10 volumes of buffer (w/v) using a Brinkmann Polytron™, setting 6, for 30 seconds. The buffer consisted of 50 mM Tris HCl at a pH of 7.5 at room temperature. The homogenate was sedimented by centrifugation (10 minutes; 50,000× g; 0 to 4° C. The supernatant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM $MgCl_2$, 2 mM $CaCl_2$ and has a pH of 7,4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [$^3$H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters using a Brandel™ multi-manifold tissue harvester. Following the initial filtration of the assay mixture, filters were washed two times with ice-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

Calculations

Specific binding (C) to the membrane is the difference between total binding in the samples containing vehicle only and membrane (A) and non-specific binding in the samples containing the membrane and cytisine (B), i.e., Specific binding=(C)=(A)−(B).

Specific binding in the presence of the test compound (E) is the difference between the total binding in the presence of the test compound (D) and non-specific binding (B), i.e., (E)=(D)−(B).

% Inhibition=(1−((E)/(C)) times 100.

The compounds of the invention, which were tested, exhibited $IC_{50}$ values of less than 1 μM.

Preparation

N-t-BOC-cytisine (N-t-BOC-cytisine)

To a one liter round bottom flask was charged 10 gm (0.053 mmol) (−)-cytisine followed by a mixture of 320 ml methylene chloride and 100 ml water. The two phase mixture was treated with 6.62 gm (0.079 mmol) sodium bicarbonate and finally 12.6 gm (0.058 mmol) di-t-butyl-dicarbonate. The reaction mixture was heated under reflux for 1.5 hours. The mixture was allowed to cool and was then diluted with brine. The organic layer was washed with brine and dried and the solvent evaporated. There was obtained 14.4 gm (94% crude) of the title product which was used directly in the next step. $^1$H NMR (CDCl$_3$, 250 MHz) δ7.28 (dd, 1H), 6.45 (d, 1H), 6.05 (d, 1H), 4.19 (m, 3H), 3.81 (dd, 1H), 3.0 (br.s, 3H), 2.41 (br.s, 1H), 1.99 (m, 2H), 1.29 (br.s, 9H) ppm, mass spectrum (thermospray) m/e 291 p+1.

EXAMPLE 1

N-t-BOC-9-bromo-1,2,3,4,5,6-hexahydro-1,5-methano-pyrido[1,2-a][1,5]diazocin-8-one (9-bromo-t-BOC cytisine)

To a 250 ml round bottom flask was added 1.87 gm (64 mmol) of t-BOC cytisine in 100 ml of methylene chloride. The solution was treated with 1.14 gm (6.4 mmol) of N-bromosuccinimide (NBS) and the reaction mixture was heated under reflux for 1.5 hours. The mixture was allowed to cool to room temperature and was diluted with water. The organic phase was separated, washed with brine, dried and the solvent was then evaporated in vacuo. The residue was flash chromatographed on silica gel eluting with methylene chloride:methanol (99.1) Three products were obtained. The least polar material was identified as the 9,11-dibromo t-BOC-cytisine. The most polar material was identified as 11-bromo-t-BOC-cytisine. The second material to elute, of intermediate polarity, was the title product 9-bromo-t-BOC-cytisine 1.34 gm (57%).

9-Bromo-t-BOC-cytisine: $^1$H NMR (CDCl$_3$, 250 MHz) δ7.68 (s, 1H) 5.99 (s, 1H), 4.28 (d, 1H), 4.20 (br, 2H), 3.89 (dd, 1H), 3.00 (br.s, 3H), 2.42 (br.s, 1H), 1.98 (br.s, 2H), 1.31 (s, 9H) ppm; mass spectrum (thermospray) m/e 369, 371.

9,11-Dibromo-t-BOC-cytisine: $^1$H NMR (CDCl$_3$, 250 MHz) δ7.88 (s, 1H), 4.38, (br.s, 2H), 4.25 (d, 1H), 3.90 (dd, 1H), 3.45 (br.s, 1H), 3.00 (br.m, 2H), 2.45 (br.s, 1H), 2.00 (br.s, 2H), 1.29 (br.s, 9H) ppm; mass spectrum (thermospray) m/e 447, 449, 451 p+1, p+2, p+4.

11-Bromo-t-BOC-cytisine: $^1$H NMR (CDCl$_3$, 250 MHz) δ7.40 (d, 1H), 6.38 (d, 1H), 4.36 (br.d, 2H), 4.15 (d, 1H), 3.82 (dd, 1H), 3.40 (br.s, 1H), 2.96 (br.m, 2H), 2.40 (br.s, 1H), 1.98 (s, 2H), 1.25 (br.s, 9H) ppm; mass spectrum (thermospray) m/e 369, 371.

EXAMPLE 2

9-Bromo-1,2,3,4,5,6hexahydro-1,5-methano-pyrido[1,2-a][1,5]diazocin-8-one Hydrochloride Salt, (9-bromo-cytisine)

A solution of the title product of Example 1 (1.28 gm; 3.5 mmol) in ethyl acetate (10 ml) was treated with a solution of 3 M HCl(g) in ethyl acetate. After 30 minutes a precipitate began to form. The reaction mixture was granulated for 24 hours to enhance the quality of the crystalline product. After filtration and drying in vacuo there was obtained 0.92 gm (87%) of the title product. An analytical sample was prepared by recrystallization from methanol-ether. The free base was prepared by treatment of the hydrochloride with methylene chloride and a 12N NaOH solution.

mp (uncorrected, Thomas-Hoover Capillary apparatus) >270° C. $^1$H NMR (free base, CDCl$_3$, 250 MHz) δ7.58 (d, 1H), 5.87 (d, 1H), 4.06 (d, 1H), 3.83 (dd, 1H), 2.92 (m, 5H), 2.27 (m, 1H), 1.87 (br.s, 2H) ppm [?].

$^{13}$C NMR (free base, CDCl$_3$, 100.1 MHz) δ160.0, 151.0, 140.7, 112.0, 104.9, 53.8. 52.9, 51.1, 35.4, 27.6, 26.1 ppm.

$^1$H NMR (hydrochloride salt, D$_2$O, 250 MHz) δ8.03 (d, 1H), 6.5 (d, 1H), 4.28 (d, 1H) 4.1 (dd, 1H), 3.5 (m, 5H), 2.88 (m, 1H), 2.15 (m 2H) ppm.

$^{13}$C NMR (hydrochloride salt, D$_2$O, 100.1 MHz) δ160.9 (C=O), 146.8 (C—Br), 143.1 (C—H) 112.1 (—C—), 109.5 (C—H), 50.0 (CH$_2$), 49.2 (CH$_2$) 48.2 (CH$_2$), 31.4, 24.8 (CH), 22.4 (CH) (CH$_2$) ppm.

Optical Rotation $[\alpha]_D$=−55.9° c=0.63, methanol mass spectrum (thermospray) m/e 269, 271. Analytical for C$_{11}$H$_{13}$BrN$_2$O. HCl.0.5H$_2$O Calc: C, 41.99, H, 4.81, N, 8.90, Found. C, 41.80, H, 5.05, N, 8.88.

The compounds of Examples 3 and 4 were prepared according to the method of Example 2.

EXAMPLE 3

11-Bromo-1,2,3,4,5,6-hexahydro-1,5-methano-pyrido[1,2-a][1,5]diazocin-8-one $^1$H NMR (CDCl$_3$, 250 MHz) δ7.4 (d, 1H), 6.36 (d, 1H), 4.05 (d, 1H), 3.89 (dd, 1H), 3.32 (br.s, 1H), 3.22–2.85 (m, 4H), 2.32 (br.s, 1H), 1.95 (br.m, 3H) ppm; mass spectrum (thermospray) m/e 269, 271.

EXAMPLE 4

9,11-Dibromo-1,2,3,4,5,6-hexahydro-1,5-methano-pyrido[1,2-a][1,5]diazocin-8-one Hydrochloride Salt $^1$H NMR (CDCl$_3$, 250 MHz) δ7.89 (s, 1H), 4.19 (d, 1H), 3.96 (dd, 1H), 3.39 (br.s, 1H), 3.23 (dd, 2H), 3.03 (dd, 2H), 2.78 (br.s, 1H), 2.41 (br.s, 1H), 2.00 (m, 2H) ppm; mass spectrum (particle beam) m/e 347, 349, 351.

EXAMPLE 5

N-t-BOC-9-chloro-1,2,3,4,5,6-hexahydro-1,5-methano-pyrido[1,2-a][1,5]diazocin-8-one (9-chloro-BOC-cytisine) and N-t-11-chloro-1,2,3,4,5,6-hexahydro-1,5-methano-pyrido[1,2-a][1,5]diazocin-8-one (11-chloro-t-BOC-cytisine)

To a 50 ml round bottom flask was added 1.19 gm (4.1 mmol) of t-BOC cytisine in 25 ml of methylene chloride. To the above solution was added 0.55 gm (4.1 mmol) of N-chlorosuccinimide and the reaction mixture was heated to reflux for 16 hrs. The reaction mixture was allowed to cool to room temperature and was then diluted with water. The organic phase was separated, washed with brine, dried and the solvent was then evaporated in vacuo. The residue was flash chromatographed on silica gel eluting with methylene chloride:methanol (98:2). Two compounds were obtained. The least polar material was identified as 9-chloro-t-BOC-cytisine (0.062 gm) and the second material to elute was 11-chloro-t-BOC-cytisine (0.914 gm).

9-chloro-t-BOC-cytisine: $^1$H NMR (CDCl$_3$, 250 MHz) δ7.46 (d, 1H), 6.04 (d, 1H), 4.26 (d, 1H), 4.19 (br.m, 2H), 3.85 (dd, 1H), 3.05 (br.m, 3H), 2.43 (br.s, 1H), 1.98 (br.s, 2H), 1.28 (br.m, 9H) ppm; mass spectrum m/e 325 p+1.

11-chloro-t-BOC-cytisine: $^1$H NMR (CDCl$_3$, 250 MHz) δ7.34 (d, 1H), 6.46 (d, 1H), 4.37 (br m, 2H), 4.19 (d, 1H), 3.84 (dd, 1H), 3.49 (br.m, 1H), 3.01 (m, 2H), 2.46 (br s, 1H). 2.00 (br.s, 2H). 1.29 (br.m, 9H) ppm; mass spectrum (particle beam) 325 p+1.

EXAMPLE 6

9-chloro-1,2,3,4,5,6-hexahydro-1,5-methano-pyrido[1,2-a][1,5]diazocin-8-one Hydrochloride Salt, (9-chloro-cytisine, HCl Salt An excess of a solution of 3 M HCl (g) in ethyl acetate was added to the least polar product of Example 5 (0063 gm, 0.19 mmol) in excess ethyl acetate. After 30 minutes a precipitate began to form. The reaction mixture was granulated for 24 hours to enhance the quality of the crystalline product. After filtration and 10 minutes drying in vacuo there was obtained 0.041 gm (95%) of the title product. $^1$H NMR (D$_2$O, 250 MHz) δ7.61 (d, 1H) 6.34 (d, 1H), 4.06 (d, 1H), 3.88 (dd, 1H), 3.25 (m, 4H), 2.66 (br.s, 1H), 1.93 (dd, 2H) ppm, mass spectrum (thermal spray) 225 p+1.

EXAMPLE 7

11-chloro-1,2,3,4,5,6-hexahydro-1,5-methano-pyrido[1,2-a][1,5]diazocin-8-one Hydrochloride Salt, (11 chloroytysine, HCl Salt)

An excess of 3 M HCl (g) in ethyl acetate was added to the more polar product of Example 5 (0.079 gm; 0.24 mmol) in ethyl acetate. After 30 minutes a precipitate began to form The reaction mixture was granulated for 24 hours to enhance the quality of the crystalline product. After filtration and brief (10 min) drying in vacuo there was obtained 0.050 gm of the title product. An analytical sample was prepared by recrystallization from methanol-ether. $^1$H NMR (CDCl$_3$, 250 MHz) δ7.30 (d, 1H), 6.43 (d, 1H), 4.08 (d, 1H), 3.89 (dd, 1H), 3.38 (br s, 1H), 3.20–2.85 (m, 4H), 2.35 (br.s, 1H), 1.95 (m, 2H) ppm; mass spectrum (thermal spray) 225 p+1.

EXAMPLE 8

9,11-Dichloro-1,2,3,4,5,6-hexahydro-1,5-methano-pyrido[1,2-a][1,5]diazocin-8-one (9,11-dichlorocytisine)

To a 10 ml round bottom flask was added 0.2 gm (0.69 mmol) of t-BOC-cytisine in 3 ml of water and the solution was cooled in an ice bath. The solution was treated with 2 ml of water saturated with chlorine gas and stirred for 1.5 hours. The reaction mixture was diluted with 2N NaOH and extracted with methylene chloride. The organic phase was washed with brine, dried and the solvent was then evaporated in vacuo. The residue (210 mg) was used directly in the reaction that follows.

To a 35 ml round bottom flask was added the above product (0.21 gm) and 12 ml of 1.1 dioxane ethyl acetate. The solution was saturated with HCl gas until a white precipitate formed The mixture was heated under reflux for 2 hours. After cooling to room temperature the reaction mixture was diluted with methylene chloride and treated with 2 N NaOH solution. The organic phase was washed with brine, dried and the solvent was evaporated in vacuo. The residue was flash chromatographed on silica gel eluting first with methylene chloride methanol (96.4) followed by elution with 95.5 methylene chloride methanol. Two compounds were obtained. The least polar (first to elute) material was identified as 9,11-dichlorocytisine (65 mg) and the second, i.e., the more polar, material to elute was 11-chlorocytisine (40 mg) (also prepared above). Both compounds were converted into the HCl salts with HCl (g) in ether:ethanol 10:1.

9,11-Dichlorocytisine: $^1$H NMR (Free Base, CDCl$_3$, 250 MHz) δ7.55 (s, 1H), 4.15 (d, 1H), 3.95 (dd, 1H), 3.38 (br.s, 1H), 3.20–2.89 (m, 4H), 2.38 (br.s, 1H), 1.95 (m, 2H) ppm; mass spectrum (particle beam) 259.

EXAMPLE 9

N-t-BOC-9methyl-1,2,3,4,5,6hexahydro-1,5-methano-pyrido[1,2-a][1,5]diazocin-8-one (N-t-BOC-9-methylcytisine)

To a 6 ml round bottom flask was added 0.132 gm (0.36 mmol) of 9-bromo-t-BOC-cytisine (the title product of Example 1) and 1.5 ml of hexamethylphosphoramide (HMPA). The solution was treated with 0.043 gm (0.057 mmol) of trans-benzylchloro-bis(triphenylphosphine) palladium and 0.153 ml (1.1 mmol) tetramethyltin. The reaction mixture was heated at 65° C. for 30 hours The dark reaction mixture was partitioned between 1:1 ethyl acetate hexanes and 50% brine. The organic phase was washed with brine, dried and the solvent evaporated. The residue was chromatographed on silica get eluting with 1% methanol in methylene chloride. There was obtained 50 mg (45%) of the title product which was used directly in the next step. $^1$H NMR (CDCl$_3$, 250 MHz) δ7.15 (d, 1H), 5.98 (d, 1H), 4.45–4.00 (m, 2H), 4.22 (d, 1H), 3.80 (dd, 1H), 2.98 (m, 3H), 2.39 (br.s, 1H). 2.09 (s, 3H), 1.92 (br.s, 2H) 1.28 (bras, 9H) ppm; mass spectrum (ACPI) 305 p+1; 205 (pt-BOC).

EXAMPLE 10

9-Methyl-1,2,3,4,5,6-hexahydro-1,5-methano-pyrido[1,2-a][1,5]diazocin-8-one Hydrochloride Salt (9-methyl-cytisine, HCl Salt)

The title product of Example 9 (0.050 gm; 0.16 mmol) in ethyl acetate was treated with an excess of a solution of 3 M HCl (g) in ethyl acetate. The reaction mixture was stirred for 1 hour and then partitioned between 2 N NaOH (aq) and methylene chloride. The organic layer was washed with brine, dried and the solvent evaporated. The residue was chromatographed on silica gel (elution with 2% methanol in methylene chloride with 0.5% ammonium hydroxide). The recovered product was then treated, in methanol-ether, with HCl gas. After filtration and 10 minutes drying in vacuo there was obtained 25 mg of the title product. An analytical sample was prepared by recrystallization from methanol-ether $^1$H NMR (Free Base, CDCl$_3$, 250 MHz) δ7.18 (d, 1H), 5.92 (d, 1H), 4.18 (d, 1H), 3.89 (dd, 1H), 3.04 (m, 4H), 2.87 (brs 1H), 2.30 (brs, 1H) 2.12 (s, 3H), 1.92 (br s, 2H) ppm: mass spectrum (APCI) 205 p+1.

EXAMPLE 11

N-t-BOC-11-methyl-1,2,3,4,5,6-hexahydro-1,5-methano-pyrido[1,2-a][1,5]diazocin-8-one (N-t-BOC-11-methyl-cytisine, HCl Salt)

To a 5 ml Wheaton flask was added 0.030 gm (0.081 mmol) of 11-bromo-t-BOC-cytisine (as prepared in Example 1) and 0.5 ml of HMPA. The solution was treated with 0.009 gm (0.01 mmol) of trans-benzylchloro-bis(triphenylphosphine)palladium and 0.035 ml (0.25 mmol) tetramethyltin. The reaction mixture was heated at 65° C. for 42 hours. The dark reaction mixture was partitioned between 1:1 ethyl acetate:hexanes and 50% brine. The organic phase was washed with brine and the solvent was then evaporated. The residue was chromatographed on silica gel eluting first with ethyl acetate followed by 1% methanol in ethyl acetate. There was obtained 20 mg (81%) of the title product which was used directly in the next step. $^1$H NMR (CDCl$_3$, 250 MHz) δ7.18 (d, 1H), 6.45 (d, $_1$H), 4.46–4.10 (m, 2H), 4.22 (d, 1H), 3.87 (dd, 1H), 3.05 (m, 3H), 2.40 (br.s, 1H), 2.12 (s, 3H), 1.98 (m, 2H) 1.26 (br.s, 9H) ppm, mass spectrum (thermospray) 305 p+1.

EXAMPLE 12

11-Methyl-1,2,3,4,5,6hexahydro-1,5-methano-pyrido[1,2-a][1,5]diazocin-8-one Hydrochloride Salt (11-methyl-cytisine, HCl Salt)

The title product of Example 11 (0.020 gm; 0.065 mmol) in ethyl acetate was treated with excess 3 M HCl (g) in ethyl acetate. The reaction mixture was stirred for 1 hour and was then partitioned between 2 N NaOH solution and methylene chloride. The organic layer was washed with brine, dried and the solvent evaporated. The residue was chromatographed on silica gel (elution with 1% methanol in methylene chloride). The recovered desired product was then treated, in methanol-ether, with HCl gas. Upon filtration and brief drying in vacuo there was obtained 6 mg of the title product. An analytical sample was prepared by recrystallization from methanol:ether 1:10. $^1$H NMR (Free Base, CDCl$_3$, 250 MHz) δ7.20 (d, 1H), 6.45 (d, 1H), 4.18 (d, 1H), 3.95 (dd, 1H), 3.05 (m, 5H), 2.31 (br.s, 1H), 2.10 (s, 3H), 1.98 (m, 2H) ppm; mass spectrum (thermospray) 205 p+1.

EXAMPLE 13

N-t-BOC-9,11-dibromo-1,2,3,4,5,6hexahydro-1,5-methano-pyrido[1,2-a][1.5]diazocin-8-one (9,11dibromo-t-BOC-cytisine)

To a 125 ml round bottom flask was added 2.24 gm (7.7 mmol) of t-BOC-cytisine in 65 ml of methanol. The solution was treated with 1.32 gm (15.8 mmol) of sodium bicarbonate and cooled to 0° C. A solution of bromine (0.810 ml 15.8 mmol) in 25 ml of methylene chloride was added dropwise and the reaction mixture was stirred for 20 minutes. The reaction mixture was concentrated and partitioned between water and methylene chloride. The organic layer was washed with saturated aqueous sodium thiosulfate solution, brine and then dried. The solvent was evaporated in vacuo. The resulting foam (3.3 gm) was used directly in the next reaction without purification. $^1$H NMR (CDCl$_3$, 250 MHz) δ7.88 (s, 1H), 4.38, (br.s, 2H), 4.25 (d, 1H) 390 (dd, $^1$H) 3.45 (br.s, 1H), 3.00 (br.m, 2H), 245 (br.s, 1H) 2.00 (br.s, 2H), 1.29 (br.s, 9H) ppm mass spectrum (thermospray) m/e 447, 449, 451 p+1. p+2. p+4.

EXAMPLE 14

N-t-BOC-9,11-dimethyl-1,2,3,4,5,6-hexahydro-1,5-methano-pyrido[1.2-a][1.5]diazocin-8-one (N-t-BOC-9,11-dimethylcytisine)

To a 5 ml Wheaton flask was added 0.139 gm (0.310 mmol) of the product of Example 13 and 1.5 ml of HMPA. The solution was treated with 0.060 gm (0.079 mmol) of trans-benzylchloro-bis(triphenylphosphine)palladium and 0.413 ml (2.98 mmol) tetramethyltin. The reaction mixture was heated at 65° C. for 12 hours. The dark reaction mixture was partitioned between 1:1 ethyl acetate:hexanes and 50% brine. The organic phase was washed with brine and dried and the solvent was then evaporated. The residue was chromatographed on silica gel eluting first with ethyl acetate followed by 1% methanol in ethyl acetate. There was obtained 44 mg (45%) of the title product which was used directly in the next step. $^1$H NMR (CDCl$_3$, 250 MHz) δ7.07 (s, 1H), 4.25 (d, 1H), 4.46–4.08 (m, 2H), 3.85 (dd, 1H), 3.05 (m, 3H), 2.40 (brs, 1H), 2.10 (s, 6H), 1.97 (br.s, 2H), 1.31 (br.s, 9H) ppm; mass spectrum (thermospray) m/e 319 p+1.

EXAMPLE 15

9,11-Dimethyl-1,2,3,4,5,6-hexahydro-1,5-methano-pyrido[1,2-a][1,5]diazocin-8-one Hydrochloride Salt (9,11-Dimethyl-cytisine, HCl Salt)

The title product from Example 14 (0.044 gm; 0.138 mmol) in ethyl acetate was treated with an excess of 3 M HCl (g) in ethyl acetate. The reaction mixture was stirred for 1 hour and was partitioned between 2 N NaOH and methylene chloride. The organic layer was washed with brine, dried and the solvent evaporated. The residue was chromatographed on silica gel (elution with 2% methanol, 1% NH$_4$OH, 97% methylene chloride). The recovered desired product was then treated, in methanol-ether, with HCl gas. After filtration and 10 minutes drying in vacuo there was obtained 12 mg of the title product. An analytical sample was prepared by recrystallization from methanol:ether. mp>270° C.

EXAMPLE 16

N-t-BOC-11-vinyl-1,2,3,4,5,6-hexahydro-1,5-methano-pyrido[1,2-a][1,5]diazocin-8-one (11-vinyl-t-BOC cytisine)

To a 6 ml round bottom flask was added 0.066 gm (0.178 mmol) of 11-bromo-t-BOC-cytisine (prepared according to Example 1) and 1.5 ml of hexamethylphosphoramide (HMPA). The solution was treated with 0.022 gm (0.03 mmol) of trans-benzylchloro-bis(triphenylphosphine) palladium and 0.161 ml (0.55 mmol) tetravinyltin. The reaction mixture was heated at 65° C. for 72 hours. The dark reaction mixture was partitioned between 1:1 ethyl acetate-:hexanes and 50% brine. The organic phase was washed with brine, dried and the solvent evaporated. The residue was chromatographed on silica gel eluting with 1% methanol in methylene chloride. There was obtained 22 mg (40%) of the title product which was used directly in the next step. $^1$H NMR (CDCl$_3$, 250 MHz) δ7.58 (d, 1H), 6.71 (dd, 1H), 6.50 (d, 1H), 5.50 (d, 1H), 5.21 (d, 1H), 4.47–4.08 (m, 2H), 4.20 (d, 1H), 3.88 (dd, 1H), 3.38 (br.s, 1H), 3.00 (br.m, 2H), 2.41 (br.s, 1H), 1.98 (br.s, 2H), 1.25 (br.s, 9H) ppm; m/e 317 p+1.

EXAMPLE 17

11-Vinyl-1,2,3,4,5,6-hexahydro-1,5-methano-pyrido[1,2-a][1,5]diazocin-8-one Hydrochloride Salt (11-vinyl-cytisine, HCl Salt)

The title product of Example 16 (0.022 gm; 0.069 mmol) in ethyl acetate was treated with an excess of 3 M HCl (g) in ethyl acetate. After 30 minutes a precipitate began to form. The reaction mixture was granulated for 24 hours to enhance the quality of the crystalline product. After filtration and 10 minutes drying in vacuo there was obtained 0.014 gm of the title product. An analytical sample was prepared by recrystallization from methanol-ether. Mass spectrum (thermospray) m/e 217 p+1.

EXAMPLE 18

N-t-BOC-11ethyl-1,2,3,4,5,6-hexahydro-1,5-methano-pyrido[1,2-a]]1,5]diazocin-8-one (N-t-BOC-11 ethyl-cytisine)

To a 4 ml round bottom flask was added 0.025 gm (0.079 mmol) of the title product of Example 16 in 1 ml of ethyl acetate. The solution was treated with 8 mg of palladium on barium sulfate catalyst and then placed under 1 atm. of hydrogen gas for 2 hours. The reaction mixture was filtered and concentrated to an oil. Chromatography on silica gel (1% methanol in methylene chloride) afforded 21 mg (80%) of the title product. $^1$H NMR (CDCl$_3$, 250 MHz) δ7.22 (d, 1H), 6.48 (d, 1H), 4.46–4.08 (m, 2H), 4.20 (d, 1H), 3.88 (dd, 1H), 3.23 (brs, 1H), 3.00 (br.m, 2H), 2.45 (m, 3H), 2.00 (brs, 2H), 1.26 (m, 12H) ppm; mass spectrum (thermospray) m/e 319 p+1.

EXAMPLE 19

11-Ethyl-1,2,3,4,5,6-hexahydro-1,5-methano-pyrido[1,2-a][1,5]diazocin-8-one Hydrochloride Salt (11-Ethyl-cytisine HCl Salt)

The product of Example 18 (0.020 gm. 0.063 mmol) in ethyl acetate was treated with an excess of 3 M HCl(g) in ethyl acetate After 30 minutes, a precipitate began to form. The reaction mixture was granulated for 24 hours to enhance the quality of the crystalline product. After filtration and 10 minutes drying in vacuo there was obtained 0.012 gm of the title product. An analytical sample was prepared by recrystallization from methanol-ether Mass spectrum (thermospray) m/e 219 P+1.

EXAMPLE 20

N-t-BOC-11-phenyl-1,2,3,4,5,6-hexahydro-1,5-methano-pyrido[1,2-a][1,5]diazocin-8-one (N-t-BOC-11-phenylcytisine)

To a 5 ml round bottom flask was added 0.076 gm (0.205 mmol) of 11-bromo-t-BOC-cytisine (prepared according to the method of Example 1) and 1.0 ml of HMPA. The solution was treated with 0.025 gm (0.03 mmol) of trans-benzylchloro-bis(triphenylphosphine)palladium and 0.208 ml (0.64 mmol) tributylphenyltin. The reaction mixture was heated at 65° C. for 48 hours. The dark reaction mixture was partitioned between 1:1 ethyl acetate:hexanes and 50% brine. The organic phase was washed with brine, dried and the solvent evaporated. The residue was chromatographed on silica gel eluting with ethyl acetate. There was obtained 64 mg (85%) of the title product which was used directly in the next step. $^1$H NMR (CDCl$_3$, 250 MHz) δ7.38 (5H, m), 7.20 (d, 1H), 6.50 (d, 1H), 4.45–3.95 (m, 2H), 4.30 (d, 1H), 3.88 (dd, 1H), 3.06 (br.s, 1H), 3.02–2.58 (m, 2H), 2.39 (br.s, 1H), 1.90 (dd, 2H), 1.37 (s, 9H) ppm: mass spectrum (thermospray) m/e 367 p+1.

EXAMPLE 21

11-Phenyl-1,2,3,4,5,6-hexahydro-1,5-methano-pyrido[1,2-a][1,5]diazocin-8one Hydrochloride Salt (N-t-BOC-11-phenylcytsine, HCl Salt)

The product from Example 20 (0.064 gm; 0.174 mmol) in ethyl acetate was treated with an excess of 3 M HCl(g) in ethyl acetate. After 30 minutes a precipitate began to form. The reaction mixture was granulated for 24 hours to enhance the quality of the crystalline product. After filtration and brief drying in vacuo there was obtained 0.043 gm of the title product. An analytical sample was prepared by recrystallization from methanol:ether. $^1$H NMR (D$_2$O, 400 MHz) δ7.38 (m, 5H), 7.20 (d, 1H), 6.50 (d, 1H), 4.1 (d, 1H), 3.95 (dd, 1H), 345 (br.s, 1H), 3.35 (d, 1H), 3.20 (dd, 1H), 2.95 (dd, 2H), 2.65 (br.s, 1H), 1.90 (dd, 2H) ppm; mass spectrum (thermospray) m/e 267 p+1.

EXAMPLE 22

9-Bromo-3-methyl-1,2,3,4,5,6-hexahydro-1,5-methano-pyrido[1,2-a][1,5]diazocin-8-one (9-Bromo-3-methylcytisine)

To a 5 ml round bottom flask was added 0.035 gm (0.130 mmol) 9-bromo cytisine (prepared previously) in 2 ml of acetone. To the resulting solution was added 0.0217 gm (0.258 mmol) potassium carbonate and 8.1 μl (0.128 mmol) of methyl iodide. The reaction mixture was heated under reflux for 1.5 hours and then evaporated in vacuo. The residue was partitioned between methylene chloride and water. The organic phase was washed with brine, dried and the solvent evaporated. Chromatography on silica gel eluting with 1% methanol in methylene chloride afforded 14 mg (38%) of the desired product. $^1$H NMR (CDCl$_3$, 250 MHz) δ7.65 (d, 1H), 5.91 (d, 1H), 4.11 (d, 1H), 3.93 (dd, 1H), 2.87 (m, 3H), 2.43 (s, 1H), 2.25 (m, 2H), 2.13 (s, 3H), 1.80 (m, 2H) ppm; mass spectrum (particle beam) m/e 283. 285.

EXAMPLE 23

3-Benzyl-9-bromo-1,2,3,4,5,6-hexahydro-1,5-methano-pyrido[1,2-a][1,5]diazocin-8-one 3-Benzyl-9-bromocytisine)

To a 10 ml round bottom flask was added 0.045 gm (0.167 mmol) 9-bromocytisine (prepared according to the method of Example 2) in 2 ml of 1,2-dichloroethane. The above solution was treated with 0.0187 gm (0.184 mmol) benzaldehyde, 9.6 μL acetic acid and 0.053 gm (0.25 mmol) sodium triacetoxyborohydride. The reaction mixture was stirred at room temperature for 2 hours and then partitioned between methylene chloride and 1 N HCl (aq). The organic phase was washed with brine, dried and the solvent evaporated in vacuo to a solid. Chromatography on silica gel eluting with 1% methanol in methylene chloride afforded 16 mg (27%) of the title product $^1$H NMR (CDCl$_3$, 250 MHz)

δ7.67 (d, 1H), 7.20 (m, 3H), 7.00 (m, 2H), 5.86 (d, 1H), 4.15 (d, 1H), 3.95 (dd, 1H), 3.43 (br.s, 2H), 2.93 (m, 2H), 2.85 (d, 1H), 2.45 (s, 1H), 2.35 (m, 2H), 1.85 (m, 2H) ppm; mass spectrum (particle beam) 359, 361.

EXAMPLE 24

3-Benzyl-9chloro-1,2,3,4,5,6hexahydro-1,5methano-pyrido[1,2-a][1,5]diazocin-8-one (3-Benzyl-9-chloro-cytisine) and 3-benzyl-11-chloro-1,2,3,4,5,6-hexahydro-1,5-methano-pyrido[1,2-a][1,5]diazocin-8-one (3-benzyl-11-chlorocytisine)

Preparation of N-benzylcytisine: To a 25 ml round bottom flask was added 0.510 gm (2.68 mmol) cytisine in 10 ml of 1,2-dichloroethane. The above solution was treated with 0.272 ml (2.68 mmol) benzaldehyde, 153 μl acetic acid and 0.852 gm (4.02 mmol) sodium triacetoxyborohydride. The reaction mixture was stirred at room temperature for 2 hours and was then partitioned between methylene chloride 1 N HCl (aq). The organic phase was washed with brine, dried and the solvent evaporated in vacuo to a solid. Chromatography on silica gel eluting with 1% methanol in methylene chloride afforded 434 mg (58%) of the title product which was used in the next step. $^1$H NMR (CDCl$_3$, 250 MHz) δ7.28 (dd, 1H), 7.15 (m, 3H), 6.98 (m, 2H), 6.52 (d, 1H), 5.92 (d, 1H), 4.10 (d, 1H), 3.88 (dd, 1H), 3.40 (dd, 2H), 2.88 (m 3H), 2.39 (brs, 1H), 2.32 (dd, 2H), 1.82 (dd, 2H) ppm.

To a 35 ml round bottom flask was added 0.434 gm (1.54 mmol) of N-benzylcytisine above, in 17 ml of methylene chloride To the above solution was added 0.207 gm (1.54 mmol) of N-chlorosuccinimide and the reaction mixture was heated under reflux for 16 hours. The reaction mixture was allowed to cool to room temperature and was then diluted with excess water. The organic phase was washed with brine, dried and the solvent evaporated in vacuo. The residue was flash chromatographed on silica gel eluting with methylene chloride:methanol (99.5:0.5) Two products were obtained. The least polar material (the first to elute) was identified as 9-chloro-N-benzylcytisine 40 mg $^1$H NMR (CDCl$_3$, 250 MHz) δ7.49 (d, 1H), 7.22 (m, 3H), 7.00 (m, 2H), 5.89 (d, 1H), 4.16 (d, 1H), 3.94(dd, 1H), 3.42 (dd, 2H), 2.90 (m, 3H), 2.45 (br.s, 1H), 2.35 (dd, 2H), 1.87 (dd, 2H) ppm; mass spectrum (thermospray) m/e 315 p+1.

The more polar, second material to elute, was 11-chloro-N-benzyl-cytisine 250 mg; $^1$H NMR (CDCl$_3$, 250 MHz) δ7.32 (d, 1H), 7.19(m, 3H), 6.98 (m, 2H), 6.51 (d, 1H), 4.05 (d, 1H), 3.88(dd, 1H), 3.45 (br.s, 3H), 3.02 (d, 1H), 2.90 (d, 1H), 2.41 (br.s, 1H), 2.30 (dd, 2H), 1.88 (br.s, 2H) ppm.

Preparation of 9-iodo-t-boc-cytisine

To a solution of 1.06 gm (3.6 mmol) t-boc cytisine in 50 ml of methanol was added 548 mg (5.5 mmol) calcium carbonate followed by the dropwise addition (over 20 min) of a solution of iodine monochloride as a 1M solution in dichloromethane (5.5 ml, 5.5 mmol). The mixture was stirred for 5 hours at room temperature and then was quenched with a mixture of aqueous thiosulfate and bicarbonate. Ethyl acetate was added to the mixture and the organic phase was separated, washed with brine and then dried and evaporated. The residue was chromatographed on silica gel, eluting with ethyl acetate hexane (7:3). There was obtained 737 mg (48%) of the desired iodo-t-boc cytisine. $^1$H NMR (CDCl$_3$, 400 MHz) 7.89 (d, J=7.5 Hz, 1H), 5.88 (br.s, 1H), 4.23 (d, J=15.6 Hz, 1H), 4.36–4.08 (br.m, 2H), 3.85 (dd, J=15.1 Hz, J=6.0 Hz, 1H), 3.00 (br.m, 3H) 2.40 (br.s, 1H), 1.95 (br.s, 2H), 1.31 (br.s, 9H) ppm; mass spectrum (thermospray) m/e 417 p+1.

Preparation of 9-morpholinocytisine

To a flame dried flask with condenser and magnetic stirrer under argon was placed 100 mg (0.27 mmole) 9bromo-tboc-cytisine and 5 ml toluene. The flask was evacuated and then placed under argon gas. The solution was treated with 0.027 ml (0.31 mmole) morpholine, 35 mg (0.36 mmole) sodium tert-butoxide and 12 mg (0.019 mmole) 2,2'-bis (diphenylphosphino)-1,1'-binaphthyl (BINAP). The mixture was evacuated briefly using a standard vacuum source and then placed once again under argon. The catalyst, bis[1,2-bis(diphenylphosphino)ethane]palladium(0) (dppe$_2$-Pd), 10 mg (0.01 mmole) was added and the reaction mixture was once again briefly placed under vacuum and then brought to atmospheric pressure under argon. The reaction mixture was heated to 130° C. for 30 min. Monitoring of the reaction progress could be accomplished by thin layer chromatography (tlc). The solvent was then concentrated in vacuo and the residue was chromatographed directly on silica gel using ethyl acetate hexane (8/2) 9-morpholino-t-boc cytisine, was obtained as an oil. $^1$H NMR (CDCl$_3$, 400 MHz)__6.63 (br s 1H). 5.99 (br.s, 1H), 4.31–4.00 (m, 2H), 4.16 (d, 1H), 3.83 (br.m, 5H), 3.23 (m, 2H), 3.04–2.91 (br m, 5H), 2.35 (br.s, 1H), 1.90 (m, 2H), 1.27 (br s, 9H) ppm mass spectrum (thermospray) m/e 376 p+1.

Removal of the t-boc protecting group was accomplished with overnight stirring at room temperature with anhydrous 3 M HCl in ethyl acetate to afford 13 mg (14%) of 9-morpholino-cytisine hydrochloride; Mass spectrum (thermospray) m/e 276 p+1.

The following derivatives were prepared through this procedure:

9-benzylamino-t-boc-cytisine: (CDCl$_3$, 400 MHz)__7.30 (m, 5H), 6.19 (br.s, 1H), 5.96 (br.s, 1H), 4.34–3.99 (m, 5H), 3.86 (m, 1H), 2.91 (m, 3H), 2.36 (br.s, 1H), 1.90 (m, 2H), 1.31 (br.s, 9H) ppm; Mass spectrum (thermospray) m/e 396 p+1.

9-benzylamino-cytisine hydrochloride: $^1$H NMR (CDCl$_3$OD, 400 MHz)__7.48 (m, 2H), 7.40 (m, 3H), 7.27 (d, J=7.5 Hz, 1H), 6.37 (d, J=7.6 Hz, 1H), 4.47 (ABq, J=13.3 Hz, 2H), 4.27 (d, J=15.8 Hz, 1H), 4.09 (m, 1H), 3.42 (m, 6H), 2.79 (br.s, 1H), 2.12 (ABq, J=13.8 Hz, 2H) ppm; Mass spectrum (thermospray) m/e 296 p+1.

9-pyrrolidino-tboc-cytisine: (CDCl$_3$, 400 MHz)__6.33 (br.s, 1H), 5.94 (br.s, 1H), 4.33–4.02 (br.m, 2H), 4.16 (m, 1H), 3.79 (dd, J=15.4 Hz, J=64 Hz, 1H), 3.46 (br.s, 2H), 3.14–2.91 (br.m, 4H), 2.35 (br.s, 1H), 1.89 (br.m, 5H), 1.31 (br.s, 9H) ppm; Mass spectrum (thermospray) m/e 360p+1.

9-pyrrolidino-cytisine: Mass spectrum (thermospray) m/e 260 p+1.

9-dimethylamino-tboc-cytisine: (CDCl$_3$, 400 MHz)__ 6.6–6.4 (br.m, 1H), 5.99 (m, 1H), 4.37–4.02 (br.m, 2H), 4.18 (br.d, 1H), 3.80 (dd, J=15.1 Hz, J=6.0 Hz, 1H), 3.06–2.92 (br.m, 3H), 2.75 (s, 6H), 2.36 (br.m, 1H), 1.91 (br.m, 3H), 1.29 (br.s, 9H) ppm; Mass spectrum (thermospray) m/e 334 p+1.

9dimethylamino-cytisine: (CDCl$_3$, 400 MHz)__6.61 (d, J=7.5 Hz, 1H), 5.92 (d, J=7.5 Hz, 1H), 4.14 (d, J=15.6 Hz, 1H), 3.89 (dd, J=15.6 Hz, J=6.6 Hz, 1H), 3.0 (br.m, 4H), 2.78 (br.s, 6H), 2.28 (br.s, 1H), 1.92 (S, 3H) ppm; Mass spectrum (thermospray) m/e 234 p+1.

HRMS (FAB) calc'd for C$_{13}$H$_{19}$N$_3$O+H 234.1606 found 234.1613

Preparation of 9-acetyl-cytisine

To a flame dried flask with condenser and magnetic stirrer under argon was placed 100 mg (0.27 mmole) 9-bromotboc-cytisine and 4 ml DMF. The flask was evacuated and then placed under argon gas. The solution was treated with 0.045 ml (0.32 mmole) triethylamine, 0.175 ml (1.35 mmole) of butylvinylether, 4.2 mg (0.0076 mmole) diphenylphosphinoferocene (dppf) and 1.5 mg (0.00075 mmole) palladium acetate. The mixture was evacuated briefly with a vacuum source and then placed once again under 1 atm argon. The reaction mixture was heated to 100° C. for 1 hr whereupon the mixture turned black. TLC analysis (9/1 ethyl acetate/hexane) indicated the reaction was not complete and 15 mg (0.067 mmole) palladium acetate and 42 mg (0.076 mmole) of dppf was added. The mixture was evacuated briefly with a vacuum source and then placed once again under argon. Heating was reinitiated at 100° C. for 0.5 hr and then the reaction mixture was allowed to cool to room temperature. The mixture was poured into 50% saturated brine solution and extracted with 1/1 ethylacetate/hexane. The extract was washed with brine and then dried and evaporated to afford 90 mg of a crude oil. Chromatography on silica gel with 9/1 ethylacetate/hexane provided 45 mg (71%) of the desired 9acetyl-t-boc-cytisine. $^1$H NMR (CDCl$_3$, 400 MHz)__8.08 (d, J=7.5 Hz, 1H), 6.17 (br.s, 1H), 4.21 (d, J=15.8 Hz, 1H), 4.36–4.09 (br.m, 2H), 3.82 (dd, J=15.8 Hz J=6.2 Hz, 1H), 3.04 (br.s, 3H), 2.63 (s, 3H), 2.45 (br.s, 1H), 1.96 (q, J=14.7 Hz, 2H), 1.3 (br.s, 9H) ppm; Mass spectrum (thermospray) m/e 333 p+1. Removal of the t-boc protecting group was accomplished with overnight stirring at room temperature with anhydrous 3 M HCl in ethyl acetate to afford a brown powder. This hydrochloride salt was converted to the free base by treatment with 25% NaOH solution and extraction with methylene chloride. After treatment with activated charcoal and filtration, the residue after evaporation of the organic phase was chromatographed on silica gel eluting with 97:2:1 methylene chloride:methanol:ammonium hydroxide to afford the desired 9acetyl-cytisine as the free base. The material was converted to the hydrochloride salt using anhydrous 3 M HCl in ethyl acetate (12.6 mg 20%). $^1$H NMR (D$_2$O, 400 MHz)__8.03 (d, J=7.7 Hz, 1H), 6.44 (d, J=7.7 Hz, 1H), 4.12 (d, J=16.0 Hz, 1H), 3.87 (dd, J=15.8 Hz, J=6.44 Hz, 1H), 3.40 (br.m, 5H), 2.72 (br.s, 1H), 2.40 (s, 3H), 1.97 (q, J=13.7 Hz, 2H) ppm; $^{13}$C NMR (free base, CDCl$_3$, 100 MHz)__ 198.0, 162.0, 158.0, 142.2, 123.0, 105.0, 53.4, 52.9, 50.2, 36.2, 31.1, 27.8, 25.9 ppm; Mass spectrum (thermospray) m/e 233p+1;

HRMS (FAB) calc'd for C$_{13}$H$_{16}$N$_2$O$_2$+H 233.1290 found 233.1286

Preparation of 9-(2-tetrahydrofuranyl)-cytisine

To a flame dried flask with condenser and magnetic stirrer under argon was placed 300 mg (0.81 mmole) 9-bromo-tboc-cytisine, 0.061 ml (0.81 mmole) of 23, dihydrofuran and 10 ml DMF. The solution was treated with 230 mg (2.4 mmole) of potassium acetate, 225 mg (0.81 mmole) tetra-n-butylammonium acetate, 5.2 mg (0.02 mmole) triphenylphosphine and 4.5 mg (0.02 mmole) of palladium acetate. The mixture was heated to 90° C. for 16 hrs under nitrogen The reaction mixture was allowed to cool to room temperature and was then partitioned between 50% brine solution and 1/1 ethyl acetate/hexane. The organic phase was washed once again with saturated brine and then dried and evaporated in vacuo. The resulting crude 9-(2-[2,3-dihydrofuran])-t-boc-cytisine was hydrogenated in 3 ml of ethanol with 10% palladium on carbon under 45 psi hydrogen gas for 5 min. The catalyst was removed and the filtrate was evaporated in vacuo to afford crude 9-(2-tetrahydrofuran)-t-boc-cytisine. The protecting group was removed by heating with 0.020 ml trifluoroacetic acid in dichloroethane for 10 min. The reaction mixture was added to water and the solution was made basic with sodium hydroxide solution. The aqueous phase was extracted with methylene chloride and the organic phase was dried and evaporated in vacuo. $^1$H NMR (CDCl$_3$, 400 MHz)__7.38 (d, J=7.1 Hz, 1H), 6.00 (m, 1H), 5.00 (m, 1H), 4.10 (dd, J=15.6 Hz, J=5.8 Hz, 1H), 4.02 (m, 1H), 3.87 (m, 2H), 2.98 (br.m, 4H), 2.86 (br.s, 1H), 2.42 (m, 1H), 2.29 (br.s, 1H), 1.92 (br.s, 4H), 1.70 (m, 2H) ppm; mass spectrum (thermospray) m/e 261 p+1. The residue (30 mg) was converted to the HCl salt (34 mg 14%) by treatment with anhydrous 3M HCl in ethyl acetate. Mass spectrum (thermospray) m/e 261 p+1.

Preparation of 9-cyanocytisine

To a flame dried flask with condenser and magnetic stirrer under argon was placed 300 mg (0.81 mmole) 9-bromo-tboc-cytisine, 124 mg (1.05 mmole) of zinc cyanide and 470 mg (0.41 mmole) of tetrakis(triphenylphosphine) palladium in 10 ml DMF. The reaction mixture was heated to 80° C. for 16 hrs and then allowed to cool to room temperature. The reaction mixture was filtered and then partitioned between 50% saturated bicarbonate solution and extracted with methylene chloride. The organic phase was washed with brine dried and evaporated in vacuo. 9cyano-t-boc-cytisine: $^1$H NMR (CDCl$_3$, 400 MHz)__7.70 (br.s, 1H), 6.15 (brs, 1H), 4.18 (br.m, 3H), 3.86 (br.m, 1H), 3.08 (br.m, 3H), 2.45 (brs, 1H), 1.99 (br.s, 2H), 1.31 (brs, 9H) ppm: Mass spectrum (thermospray) m/e 316 p+1. The protecting group was removed by heating with 10 equivalents of trifluoroacetic acid in dichloroethane for 1 hr. The mixture was cooled to room temperature and then partitioned between water and methylene chloride. The aqueous phase was made basic to pH –12 with sodium hydroxide. The organic phase was separated and washed with saturated brine solution and dried and evaporated. 9-cyanocytisine was converted to the hydrochloride salt by treatment with anhydrous 3M HCl in ethylacetate 102 mg (51%) $^1$H NMR (CD$_3$OD, 400 MHz)__ 8.02 (d, J=7.5 Hz, 1H), 6.51 (d, J=7.6 Hz, 1H), 4.24 (d, J=16.2 Hz, 1H), 4.03 (dd, J=16.2 Hz, J=6.6 Hz, 1H), 3.48 (br.m, 5H), 2.80 (br.s, 1H), 2.12 (q, J=13.5 Hz, 2H) ppm; IR (film) λ__2221, 1642, 1555 cm$^{-1}$; Mass spectrum (thermospray) m/e 216 p+1.

HRMS (FAB) calc'd for C$_{12}$H$_{13}$N$_3$O+H 216.1137 found 216.1134

Preparation of 9-(2-propenyl)cytisine, 9-(2-propyl) cytisine and 9-acetylcytisine 2-propenylboronic Acid To a solution of 2-bromopropene (2.6 ml, 0.031 mol) in 50 ml anhydrous THF at –78° C. was added 12.6 ml (0.032 mol) n-butyl lithium in hexanes dropwise (0.5 ml min). The reaction mixture was stirred at –78° C. for 0.5 hours and then treated with 10.5 ml (0.045 mole) trisopropylborate over 5 minutes. The reaction mixture was stirred for 2 hours and then warmed slowly to room temperature. The reaction was quenched with 2N HCl until pH=1 and concentrated to ½ volume before diluting with ethyl acetate. The organic phase was extracted with 1N NaOH three times and then the pH was adjusted to 1.0 with conc HCl at 0° C. The aqueous layer was extracted with ethyl acetate, washed with brine dried and evaporated in vacuo to afford 0.88 gm (33%). The crude product was used directly in the next step. $^1$H NMR (CDCl$_3$, 400 MHz)__6.11 (br.s, 1H), 5.83 (br.s, 1H), 1.88 (s, 3H) ppm.

9-(2-propenyl)-tboc-cytisine

A mixture of 9-bromo-tboc-cytisine 1.0 gm (0.0027mol) and 1.2 gm (0.014 mol) 2-propenylboronic acid was dissolved in 86.0 ml ethanol-water (9:1) together with 0.94 gm (0.0089 mol) sodium carbonate and 0.1 gm (0.086 mmol) tetrakis(triphenyl-phosphine)palladium. The reaction mixture was heated under reflux and under argon gas for 18 hours. After cooling to room temperature, the reaction mixture was filtered and concentrated. The residue was redissolved in ethyl acetate and washed with water and then brine. The crude material, obtained by evaporation, was pad-chromatographed on silica gel using a gradient solvent system for elution. Thus the column was flushed with 50% ethyl acetate/hexane followed by 80% ethyl acetate/hexane and finally 1% methanol ethyl acetate to afford 9-(2-propenyl)-tboc-cytisine after concentration and drying in vacuo. (0.93 gm, quant). $^1$H NMR (CDCl$_3$, 400 MHz)__7.26 (m, 1H), 6.04 (br.s, 1H), 5.61 (s, 1H), 5.12 (s, 1H), 4.37–4.06 (br.m, 2H), 4.19 (d, J=15.6 Hz, 1H), 3.81 (dd, J=15.6 Hz, J=6.4 Hz, 1H), 2.98 (br.m, 3H), 2.39 (br.s, 1H), 2.05 (s, 3H), 1.92 (m, 2H), 1.29 (br.s, 9H) ppm; mass spectrum (thermospray) m/e 331 p+1. The protecting group was removed by treatment with 5 ml trifluoroacetic acid in 100 ml dichloroethane under reflux for 45 min. The reaction mixture was cooled to room temperature and was then washed with 2N sodium hydroxide solution followed by brine. The organic layer was dried over sodium sulfate and evaporated to furnish 9-(2-propenyl)cytisine $^1$H NMR (CDCl$_3$, 400 MHz)__7.29 (d, J=7.3 Hz, 1H), 5.99 (d, J=7.3 Hz, 1H), 5.71 (t, J=1 Hz, 1H), 5.17 (t, J=1 Hz, 1H), 4.15 (d, J=15.6 Hz, 1H), 3.88 (dd, J=15.6 Hz, J=6.5 Hz, 1H), 3.14–2.99 (br.m, 4H), 2.90 (br.s, 1H), 2.34 (br.s, 1H), 2.10 (s, 3H), 1.94 (br.s, 2H) ppm; Mass spectrum (thermospray) m/e 231 p+1.

HRMS (FAB) calc'd for $C_{14}H_{18}N_2O$+H 231.1497. found 231 1483

9-acetyl-tboc-cytisine 9-(2-propenyl)-tboc-cytisine from above (501 mg, 1.5 mmol) in 45 ml of dioxane was treated with 1.9 gm (0.19 mmol) osmium tetroxide (2.5% sol in t-butanol) and stirred at room temperature for 4 hours. The green reaction mixture was treated with water (5 ml) and 350 mg (3 mmol) of n-methylmorpholine N-oxide. After 0.5 hours, the solution was treated with 680 mg (3.2 mmol) sodium periodate and the reaction mixture was stirred overnight. The color of the mixture was now light yellow and a precipitate had been formed. The reaction mixture was treated with water and 2 ml 2N HCl and extracted with ethyl acetate. The organic phase was washed with brine and then dried and evaporated. The residue was passed through a pad of silica gel eluting with 1% methanol/ethyl acetate to afford after evaporation 433 mg (86%) of acetyl-t-boc-cytisine as a solid. $^1$H NMR (CDCl$_3$, 400 MHz)__8.08 (d, J=7.5 Hz, 1H), 6.17 (br.s, 1H), 4.21 (d, J=15.8 Hz, 1H), 4.36–4.09 (br.m, 2H), 3.82 (dd, J=15.8 Hz, J=6.2 Hz, 1H), 3.04 (br.s, 3H), 2.63 (s, 3H), 2.45 (br.s, 1H), 1.96 (q, J=14.7 Hz, 2H), 1.3 (br.s, 9H) ppm; mass spectrum (thermospray) m/e 333 p+1.

9-(2propyl)cytisine 9-(2-propenyl)-tboc-cytisine (418 mg, 1.2 mmol) in 40 ml methanol was treated with 209 mg of 10% palladium on carbon. The mixture was placed under 35 psi hydrogen pressure for 7 hours in a Parr shaker. The reaction mixture was then filtered and evaporated in vacuo. The residue was partitioned between ethyl acetate and brine. The organic phase was dried and evaporated to afford 305 mg (73%) of the desired product NMR (CDCl$_3$, 400 MHz)__7.11 (d, J=7.1 Hz, 1H), 6.03 (br.s, 1H), 4.18 (d, J=15.6 Hz, 1H), 4.37–4.06 (br.m, 2H), 3.81 (dd, J=15.5 Hz, J=6.6 Hz, 1H), 3.20–2.80 (br.m, 4H), 2.38 (br.s, 1H), 1.93 (q, J=12.9 Hz, 2H), 1.30 (br.s, 9H), 1.13 (obsc.d, 6H) ppm; mass spectrum (thermospray) m/e 333 p+1. The protecting group was removed by treatment with 5 ml trifluoroacetic acid in 100 ml dichloroethane under reflux for 45 min. The reaction mixture was cooled to room temperature and was then washed with 2N sodium hydroxide solution followed by brine. The organic layer was dried over sodium sulfate and evaporated. The hydrochloride salt was prepared by treatment of the residue with anhydrous 3N HCl in ethyl acetate to furnish 9-(2-propyl)cytisine $^1$H NMR (D$_2$O, 400 MHz) 7.34 (d, J=7.3 Hz, 1H), 6.33 (d, J=7.3 Hz, 1H), 4.02 (d, J=15.2 Hz, 1H), 3.83 (dd, J=15.8 Hz, J=6.6 Hz, 1H), 3.23 (br.m, 5H), 2.88 (spt, 1H), 2.64 (brs, 1H), 1.93 (q, J=13.7 Hz, 2H), 0.96 (d, J=7.0 Hz, 6H) ppm; mass spectrum (thermospray) m/e 233 p+1.

HRMS (FAB) calc'd for $C_{14}H_{20}N_2O$+H 233.1654 found 233.1658

9-carbomethoxycytisine

A mixture of 600 mg (1.62 mmol) 9-bromo-N-tboc-cytisine in 40 ml of methanol was treated with 10 mg (0.04 mmol) palladium acetate, 20 mg (0.05 mmol) 1,3-diphenylphosphinylpropane (dppp) and 917 mg (9.2 mmol) potassium bicarbonate. The reaction mixture was placed in a Parr apparatus and then degassed using vacuum. The container was then placed under 16 psi carbon monoxide pressure and slowly heated to 70° C. The reaction was agitated for 16 hours while the pressure rose to 36 psi. The reaction mixture was cooled, purged with a nitrogen atmosphere and then filtered. The filtrate was evaporated. The residue was partitioned between ethyl acetate and water, and the organic phase was washed with brine cried and evaporated. There was obtained 485 mg (86%) of 9-carbomethoxy-N-tboc-cytisine. $^1$H NMR (CDCl$_3$, 400 MHz)__8.12 (d, J=7.3 Hz, 1H), 6.12 (d, J=7.5 Hz, 1H), 4.18 (d, J=16 Hz, 1H), 4.4-4.1 (br.m, 2H), 3.85 (obsc, 1H), 3.87 (s, 3H), 3.05 (br s, 3H), 2.45 (br s, 1H), 1.95 (obsc q, 2H) 1.31 (br s, 9H) ppm; mass spectrum (thermospray) m/e 349 p+1. The protecting group was removed by treatment of 67 mg of the ester with 0.5 ml trifluoroacetic acid in 10 ml dichloroethane under reflux for 20 minutes. The reaction mixture was cooled to room temperature and treated with aq hydroxide solution and methylene chloride. The organic phase was washed with brine and then dried and evaporated in vacuo. The residue was dissolved in ethyl acetate and treated with anhydrous 3M HCl in ethyl acetate to afford 9-carbomethoxycytisine hydrochloride (11 mg). $^1$H NMR (D$_2$O, 400 MHz)__8.11 (d, J=7.7 Hz, 1H), 6.43 (d, J=7.7 Hz, 1H), 4.12 (d, J=16 Hz, 1H), 3.87 (dd, J=16 Hz, J Hz, 1H), 3.67 (s, 3H), 3.40 (br.m, 5H), 2.70 (brs, 1H), 1.96 (q, J=Hz, 2H) ppm; mass spectrum (thermospray) m/e 249 p+1;

HRMS (FAB) calc'd for $C_{13}H_{16}N_2O_3$+H 249.1239. found 249.1231

Preparation of N-t-boc-9-cytisinecarboxaldehyde

A solution of 527 mg (1.5 mmol) 9 carbomethoxy-N-tboc-cytisine in 40 ml of methylene chloride at −78° C. was treated with 1.67 ml (1.67 mmol) of a 1M solution of DIBAL-H in methylene chloride and stirred for 3 hours at low temperature. The reaction mixture was quenched with 2 N HCl and warmed to 0° C. The organic phase was washed with brine dried and evaporated. The residue was chromatographed on silica gel using a gradient elution consisting of 1.5–3% MeOH in ethyl acetate to afford 292 mg (60%) of the desired aldehyde.

HRMS (FAB) calc'd for $C_{12}H_{14}N_2O_2$+H 219.1134. found 219.1123

Preparation of 9-(2-methoxyphenyl)cytisine

A solution of 9-bromo-tboc-cytisine (251 mg (0.68 mmol)] and 114 mg (0.75 mmol) o-methoxyphenylboronic acid in 18 ml ethanol-water (9:1) was treated with 186 mg (1.7 mmol) sodium carbonate and then placed under vacuum. The evacuated flask was brought to 1 atm with argon and then treated with 17 mg (0.015 mmol) tetrakis (triphenylphosphine)palladium (0). The flask was evacuated briefly and then placed under 1 atm argon and heated under reflux for 6 hours. The dark reaction mixture was allowed to cool to room temperature before filtering of the solid mass. The filtrate was extracted with ethyl acetate and the organic layer was washed with brine, dried over sodium sulfate and evaporated in vacuo. The residue was chromatographed on a silica pad eluting first with 8.2 ethyl acetate hexane followed by 1% methanol in ethyl acetate The product 9-(2-methoxyphenyl)-t-boc-cytisine (250 mg, 93%) was obtained as a white solid The protecting group was removed by treatment with anhydrous 3M HCl in ethyl acetate at room temperature followed by recrystallization from methanol ether to afford 204 mg (98%) of the hydrochloride salt.

HRMS (FAB) calc'd for $C_{18}H_{20}N_2O_2$+H 297.1603. found 297.1584

Preparation of 9-(2,6-difluorophenyl)cytisine

A solution of 9-bromo-tboc-cytisine (740 mg (2.0 mmol)] and 1.2 ml (5.2 mmol) triisopropylborate in 50 ml THF was cooled to −78° C. before dropwise addition of 0.85 ml (2.1 mmol) of 2.5 M n-butyl lithium. The reaction mixture was stirred at −78° C. for 3 hours and 2 hours at 0° C. before quenching with 2N HCl. Most of the THF was evaporated and the residuals were extracted with ethyl acetate. The organic layer was washed with brine, dried over sodium sulfate and evaporated in vacuo. The resulting solid was triturated with a minimum amount of ether to afford 590 mg (88%) of N-tboc-cytisine-9-boronic acid product as a mixture of boronic acid and anhydrides mass spectrum (thermospray) m/e 335 p+1.

A mixture of N-tboc-cytisine-9-boronic acid [100 mg (0.3 mmol)] and 57.6 mg (0.3 mmol) 2,6-difluoro-1-bromobenzene was prepared in 10 ml ethanol-water (9:1) containing 140 mg (1.3 mmol) of sodium carbonate. The flask was evacuated briefs and then placed under 1 atm argon. The mixture was treated with 14 mg (0.012 mmol) tetrakis (triphenylphosphine)palladium (0), briefly evacuated and then was paced under 1 atm argon and heated to reflux for 16 hours. The reaction mixture was filtered and evaporated in vacuo. The residue was taken up in ethyl acetate and water and the organic phase was washed with brine, dried and evaporated. The crude product was pad chromatographed on silica eluting first with 8:2 ethyl acetate hexane followed by 1% methanol in ethyl acetate. This afforded 51 mg (40%) of 94(2,6difluorophenyl)-N-t-boc-cytisine. The protecting group was removed by treatment with 0.1 ml trifluoroacetic acid in 5 ml methylene chloride under reflux for 3 hours. The reaction mixture was cooled to room temperature and treated with aq sodium bicarbonate solution. The organic phase was washed with brine and then dried and evaporated in vacuo. The residue was dissolved in ethyl acetate and treated with anhydrous 3M HCl in ethyl acetate to afford 9-(2,6difluorophenyl)cytisine hydrochloride (21 mg). mass spectrum (thermospray) m/e 303 p+1.

The following compounds were prepared as described above
9-[2-(1,1,1-trifluoromethylpropenyl)cytisine HRMS (FAB) calc'd for $C_{14}H_{15}F_3N_2O$+H 285 1215. found 285 1203
9-(4-methoxyphenyl)cytisine mass spectrum (thermospray) m/e 297 p+1.
9-(2-ethoxy-5-methylphenyl)cytisine HRMS (FAB) calc'd for $C_{20}H_{24}N_2O_2$+H 325 1916 found 325.1897
9-(2-benzofuranyl)cytisine HRMS (FAB) calc'd for $C_{19}H_{18}N_2O_2$+H 3071 found 307.1451
9-(2-thienyl)cytisine HRMS (FAB) calc'd for $C_{15}H_{16}N_2OS$+H 273 1062 found 273 1055
9-(3-thienyl)cytisine HRMS (FAB) calc'd for $C_{15}H_{16}N_2OS$+H 273 1062 found 273.1036
9-[3-(4-methylthienyl)]cytisine HRMS (FAB) calc'd for $C_{16}H_{18}N_2OS$+H 287.1218 found 287.1213
9-[2-(3-methylthienyl)]cytisine HRMS (FAB) calc'd for $C_{16}H_{18}N_2OS$+H 287 1218 found 287.1223
9-[3-(2-fluoropyridyl)]cytisine HRMS (FAB) calc'd for $C_{16}H_{16}FN_3O$+H 286.1356 found 286.1338
9-(2-pyridyl)cytisine mass spectrum (thermospray) m/e 268 p+1
9-(2-furanyl)cytisine HRMS (FAB) calc'd for $C_{15}H_{16}N_2O_2$+H 257.1290 found 257.1305
9-(3-furanyl)cytisine HRMS (FAB) calc'd for $C_{15}H_{16}N_2O_2$+H 257.1290 found 257.1299
9-(2-trifluoromethylphenyl)cytisine mass spectrum (thermospray) m/e 335 p+1
9-(4trifluoromethylphenyl)cytisine HRMS (FAB) calc'd for $C_{18}H_{17}F_3N_2O$+H335.1371 found 335.1367
9-phenylcytisine mass spectrum (thermospray) m/e 267 p+1
11-phenylcytisine mass spectrum (thermospray) m/e 267 p+1
9-(2-methylphenyl)cytisine HRMS (FAB) calc'd for $C_{18}H_{20}N_2O$+H 281.1654 found 281.1632
9-(3-acetylphenyl)cytisine HRMS (FAB) calc'd for $C_{19}H_{20}N_2O_2$+H 309.1603 found 309.1617
9-(2chlorophenyl)cytisine HRMS (FAB) calc'd for $C_{17}H_{17}ClN_2O$+H 301.1108 found 301.1114
9-(3,4-dichlorophenyl)cytisine HRMS (FAB) calc'd for $C_{17}H_{16}C_{12}N_2O$+H 335 0718 found 335.0692
9-(2-fluorophenyl)cytisine HRMS (FAB) calc'd for $C_{17}H_{17}FN_2O$+H 285.1403 found 285.1379
9-(4-fluorophenyl)cytisine HRMS (FAB) calc'd for $C_{17}H_{17}FN_2O$+H 285 1403 found 285.1397
9-(3-fluorophenyl)cytisine HRMS (FAB) calc'd for $C_{17}H_{17}FN_2O$+H 285 1403 found 285.1401
9-(3,5-difluorophenyl)cytisine HRMS (FAB) calc'd for $C_{17}H_{16}F_2N_2O$+H 303 1309 found 303.1295
9-(2,4-difluorophenyl)cytisine HRMS (FAB) calc'd for $C_{17}H_{16}F_2N_2O$+H 303.1309 found 303.1297
9-(2-fluoro-4-chlorophenyl)cytisine HRMS (FAB) calc'd for $C_{17}H_{16}FClN_2O$+H 319.1013 found 319.1009
9-(2-fluoro-4-methoxyphenyl)cytisine mass spectrum (thermospray) m/e 315 p+1
9-(2,5difluorophenyl)cytisine HRMS (FAB) calc'd for $C_{17}H_{16}F_2N_2O$+H 303.1309 found 303.1335
9-(2-thiazoyl)cytisine mass spectrum (thermospray) m/e 274 p+1

What is claimed is:

1. A pyridone-fused azabicyclic compound of the formula

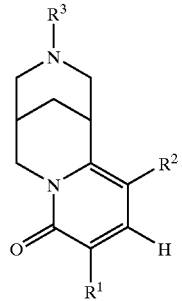

I or an enantiomer, diastereomer, stereoisomer, pharmaceutically acceptable salt or prodrug thereof, wherein $R^1$ is selected from a) halo, $CF_3$, hydroxy, $(C_1-C_6)$alkoxy, $CH_2OH$, $(C_6-C_{10})$ aryl, $(C_5-C_9)$heteroaryl;
$(C_2-C_6)$alkynyl-R and —C(O)R wherein R is H, $(C_1-C_6)$ alkyl, $(C_6-C_{10})$aryl, $(C_5-C_9)$heteroaryl and benzyl, substituted alkyl, aryl and benzyl;
cyano;
—S(O)$_n$R, wherein R is H, $(C_1-C_6)$ alkyl, aryl, substituted alkyl, and n is 0,1,2;
$(C_1-C_6)$alkyl, $(C_2-C_6)$alkenyl, amino, di-[$(C_1-C_6)$ alkyl]amino, $(C_1-C_6)$monoalkylamino, $(C_6-C_{10})$ arylamino, $(C_3-C_8)$cycloalkylamino, heteroarylamino, cycloheteroalkyamino and CON$(R^5)_2$ wherein each $R^5$ is selected from hydrogen, $(C_1-C_6)$alkyl and $(C_6-C_{10})$aryl; and b) $CO_2R$ wherein R is selected from H, $(C_1-C_6)$alkyl, phenyl and benzyl; and wherein any of the alkyl, alkenyl, aryl, cycloalkyl, cycloheteroalkyl and heteroaryl groups in a) and b are optionally substituted with one or more substituents selected from halogen, $C_1-C_6$alkyl, $(C_6-C_{10})$aryl, hydroxy, hydroxymethyl, CHO and $CO_2R$ wherein R is as described above;

$R^2$ is H; and $R^3$ is selected from H, optionally substituted benzyl and methyl;

with the proviso that when $R^3$ is H, $R^1$ cannot be bromo, and when $R^3$ is methyl, $R^1$ cannot be halo, $(C_1-C_7)$ alkoxy or $(C_1-C_6)$ alkyl.

2. The compound according to claim 1 wherein aryl is optionally substituted phenyl or naphthyl, cycloalkyl is optionally substituted and optionally unsaturated cyclopentyl or cyclohexyl, heteroaryl is selected from optionally substituted thienyl, furyl, pyrano, pyrrolo, imidazolyl, oxazolyl, thiazolyl, oxadiazolyl, thiadiazolyl, tetrazolyl, triazolyl, pyrazinyl and pyridyl and cycloheteroalkyl is selected from optionally substituted pyrrolidinyl, piperidinyl and tetrahydrofuryl and tetrahydropyrano.

3. The compound according to claim 1, wherein $R^3$ is selected from H, benzyl or methyl and $R^1$ is selected from halo, $(C_1-C_6)$alkyl, cyano, $(C_6-C_{10})$aryl, $(C_5-C_9)$heteroaryl, $(C_2-C_6)$alkenyl, $(C_2-C_6)$alkynyl-R and —C(O)R wherein R is H, $(C_1-C_6)$ alkyl, $(C_5-C_{10})$ aryl and $(C_5-C_9)$heteroaryl.

4. The compound according to claim 3, wherein $R^1$ is selected from H, ethyl, methyl, phenyl, vinyl, fluoro, bromo, chloro, isopropyl, tert-butyl, trifluoromethyl, acetyl, propanoyl, 2,2-dimethylpropanoyl, 2-methylpropanoyl, butanoyl, pentanoyl, cyano, di-[$(C_1-C_6)$alkyl]amino, $(C_1-C_6)$monoalkylamino, $(C_6-C_{10})$arylamino, $(C_3-C_8)$ cycloalkylamino, heteroarylamino, cycloheteroalkyamino and CON$(R^5)_2$ wherein each $R^5$ is selected from hydrogen, $(C_1-C_6)$alkyl and $(C_6-C_{10})$aryl; $(C_6-C_{10})$aryl and $(C_5-C_9)$ heteroaryl wherein the aryl and heteroaryl groups are optionally substituted with one or more substituents selected from halogen, $(C_1-C_6)$alkyl, $(C_6-C_{10})$aryl, hydroxy, hydroxymethyl, CHO and $CO_2R$.

5. The compound according to claim 1, wherein $R^1$ is selected from halo, cyano, optionally substituted $(C_1-C_6)$ alkyl, $(C_2-C_6)$alkenyl, amino, di-[$(C_1-C_6)$alkyl]amino, $(C_1-C_6)$monoalkylamino, $(C_6-C_{10})$arylamino, $(C_3-C_8)$ cycloalkylamino, heteroarylamino, cycloheteroalkyamino and CON$(R^5)_2$ wherein each $R^5$ is selected from hydrogen, $(C_1-C_6)$alkyl and $(C_6-C_{10})$aryl; —C(O)R wherein R is H, $(C_1-C_6)$ alkyl, $(C_6-C_{10})$ aryl and $(C_5-C_9)$heteroaryl; $(C_6-C_{10})$aryl or $(C_5-C_9)$heteroaryl wherein the substituents are described above.

6. The compound according to claim 5, wherein $R^1$ is selected from bromo, chloro, ethyl, methyl, fluoro, vinyl and phenyl, isopropyl, tert-butyl, trifluoromethyl, acetyl, propanoyl, 2,2-dimethylpropanoyl, 2-methylpropanoyl, butanoyl, pentanoyl, cyano, 2,4-difluorophenyl, 2-fluorophenyl, 2- and 3-thienyl, dimethylamino and $R^3$ is selected from hydrogen, benzyl, methyl.

7. A compound of the formula

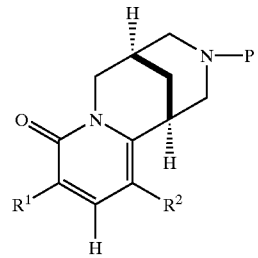

II wherein P is selected from t-butoxycarbonyl (t-BOC), acetyl, benzoyl, trifluoroacetyl and carbobenzyloxy (CBZ) and $R^1$ and $R^2$ are each independently selected from H, $(C_1-C_6)$alkyl, $(C_2-C_6)$alkenyl and $(C_6-C_{10})$ aryl with the proviso that $R^1$ and $R^2$ are not both hydrogen.

8. The compound according to claim 7 wherein $R^1$ and $R^2$ are each independently selected from H, ethyl, methyl, vinyl and phenyl.

9. A pharmaceutical composition for use in reducing nicotine addiction or to aid in the cessation or lessening of tobacco use in a mammal comprising an amount of a compound of claim 1, or a pharmaceutically acceptable salt or prodrug thereof, effective in reducing nicotine addiction, and for the prevention and treatment of withdrawal symptoms caused by cessation of chronic or long term use of tobacco products and a pharmaceutically acceptable carrier.

10. A method for reducing nicotine addiction in a mammal, comprising administering to a mammal, in need thereof, an amount of a compound of claim 1, or a pharmaceutically acceptable salt or prodrug thereof, effective in reducing nicotine addiction and also for the treatment or prevention of withdrawal symptoms caused by cessation of chronic or long term use of tobacco products.

11. The method of claim 10 wherein the compound of formula I is selected from 9-morpholino-1,2,3,4,5,6-hexahydro-1,5-methano-pyrido[1,2a][1,5]diazocin-8-one;

9-benzylamino-1,2,3,4,5,6-hexahydro-1,5-methano-pyrido[1,2a][1,5]diazocin-8-one;

9-pyrrolidino-1,2,3,4,5,6-hexahydro-1,5-methano-pyrido[1,2a][1,5]diazocin-8-one;

9-dimethylamino-1,2,3,4,5,6-hexahydro-1,5-methano-pyrido[1,2a][1,5]diazocin-8-one;

9-acetyl-1,2,3,4,5,6-hexahydro-1,5-methano-pyrido[1,2a][1,5]diazocin-8-one;

9-(2-tetrahydrofuranyl)-1,2,3,4,5,6-hexahydro-1,5-methano-pyrido[1,2a][1,5]diazocin-8-one;

9-iodo-1,2,3,4,5,6-hexahydro-1,5-methano-pyrido[1,2a][1,5]diazocin-8-one;

9-cyano-1,2,3,4,5,6-hexahydro-1,5-methano-pyrido[1,2a][1,5]diazocin-8-one;

9-ethynyl-1,2,3,4,5,6-hexahydro-1,5-methano-pyrido[1,2a][1,5]diazocin-8-one;

9-(2-propenyl)-1,2,3,4,5,6-hexahydro-1,5-methano-pyrido[1,2a][1,5]diazocin-8-one;

9-(2-propyl)-1,2,3,4,5,6-hexahydro-1,5-methano-pyrido[1,2a][1,5]diazocin-8-one;

9-carbomethoxy-1,2,3,4,5,6-hexahydro-1,5-methano-pyrido[1,2a][1,5]diazocin-8-one;

9-carboxyaldehyde-1,2,3,4,5,6-hexahydro-1,5-methano-pyrido[1,2a][1,5]diazocin-8-one;

9-(2-methoxyphenyl)-1,2,3,4,5,6-hexahydro-1,5-methano-pyrido[1,2a][1,5]diazocin-8-one;

9-(2,6-difluorophenyl)-1,2,3,4,5,6-hexahydro-1,5-methano-pyrido[1,2a][1,5]diazocin-8-one;

9-[2-(1,1,1-trifluoromethylpropenyl)-1,2,3,4,5,6-hexahydro-1,5-methano-pyrido[1,2a][1,5]diazocin-8-one;

9-(4-methoxyphenyl)-1,2,3,4,5,6-hexahydro-1,5-methano-pyrido[1,2a][1,5]diazocin-8-one;

9-(2-ethoxy-5-methylphenyl)-1,2,3,4,5,6-hexahydro-1,5-methano-pyrido[1,2a][1,5]diazocin-8-one;

9-(2-benzofuranyl)-1,2,3,4,5,6-hexahydro-1,5-methano-pyrido[1,2a][1,5]diazocin-8-one;

9-(2-thienyl)-1,2,3,4,5,6-hexahydro-1,5-methano-pyrido[1,2a][1,5]diazocin-8-one;

9-(3-thienyl)-1,2,3,4,5,6-hexahydro-1,5-methano-pyrido[1,2a][1,5]diazocin-8-one;

9-[3-(4-methylthienyl)]-1,2,3,4,5,6-hexahydro-1,5-methano-pyrido[1,2a][1,5]diazocin-8-one;

9-[2-(3-methylthienyl)]-1,2,3,4,5,6-hexahydro-1,5-methano-pyrido[1,2a][1,5]diazocin-8-one;

9-[3-(2-fluoropyridyl)]-1,2,3,4,5,6-hexahydro-1,5-methano-pyrido[1,2a][1,5]diazocin-8-one;

9-(2-pyridyl)-1,2,3,4,5,6-hexahydro-1,5-methano-pyrido[1,2a][1,5]diazocin-8-one;

9-(2-furanyl)-1,2,3,4,5,6-hexahydro-1,5-methano-pyrido[1,2a][1,5]diazocin-8-one;

9-(3-furanyl)-1,2,3,4,5,6-hexahydro-1,5-methano-pyrido[1,2a][1,5]diazocin-8-one;

9-(2-trifluoromethylphenyl)-1,2,3,4,5,6-hexahydro-1,5-methano-pyrido[1,2a]-[1,5]diazocin-8-one;

9-(4-trifluoromethylphenyl)-1,2,3,4,5,6-hexahydro-1,5-methano-pyrido[1,2a][1,5]diazocin-8-one;

9-phenyl-1,2,3,4,5,6-hexahydro-1,5-methano-pyrido(1,2a][1,5]diazocin-8-one;

9-(2-methylphenyl)-1,2,3,4,5,6-hexahydro-1,5-methano-pyrido[1,2a][1,5]diazocin-8-one;

9-(3-acetylphenyl)-1,2,3,4,5,6-hexahydro-1,5-methano-pyrido[1,2a][1,5]diazocin-8-one;

9-(2-chlorophenyl)-1,2,3,4,5,6-hexahydro-1,5-methano-pyrido[1,2a][1,5]diazocin-8-one;

9-(3,4-dichlorophenyl)-1,2,3,4,5,6-hexahydro-1,5-methano-pyrido[1,2a][1,5]diazocin-8-one;

9-(2-fluorophenyl)-1,2,3,4,5,6-hexahydro-1,5-methano-pyrido[1,2a][1,5]diazocin-8-one;

9-(4-fluorophenyl)-1,2,3,4,5,6-hexahydro-1,5-methano-pyrido[1,2a][1,5]diazocin-8-one;

9-(3-fluorophenyl)-1,2,3,4,5,6-hexahydro-1,5-methano-pyrido[1,2a][1,5]diazocin-8-one:

9-(3,5-difluorophenyl)-1,2,3,4,5,6-hexahydro-1,5-methano-pyrido[1,2a][1,5]diazocin-8-one;

9-(2,4-difluorophenyl)-1,2,3,4,5,6-hexahydro-1,5-methano-pyrido[1,2a][1,5]diazocin-8-one;

9-(2-fluoro-chlorophenyl)-1,2,3,4,5,6-hexahydro-1,5-methano-pyrido[1,2a][1,5]diazocin-8-one;

9-(2-fluoro-4-methoxyphenyl)-1,2,3,4,5,6-hexahydro-1,5-methano-pyrido[1,2a][1,5]diazocin-8-one;

9-(2,5-difluorophenyl)-1,2,3,4,5,6-hexahydro-1,5-methano-pyrido[1,2a][1,5]diazocin-8-one 9-(2-thiazoyl)-1,2,3,4,5,6-hexahydro-1,5-methano-pyrido[1,2a][1,5]diazocin-8-one;

9-chloro-1,2,3,4,5,6-hexahydro-1,5-methano-pyrido[1,2-a][1,5]diazocin-8-one;

9-flouro-1,2,3,4,5,6-hexahydro-1,5-methano-pyrido[1,2-a][1,5]diazocin-8-one;

9-ethyl-1,2,3,4,5,6-hexahydro-1,5-methano-pyrido[1,2-a][1,5]diazocin-8-one;

9-methyl-1,2,3,4,5,6-hexahydro-1,5-methano-pyrido[1,2-a][1,5]diazocin-8-one;

9-phenyl-1,2,3,4,5,6-hexahydro-1,5-methano-pyrido[1,2-a][1,5]diazocin-8-one;

9-vinyl-1,2,3,4,5,6-hexahydro-1,5-methano-pyrido[1,2-a][1,5]diazocin-8-one;

3-benzyl-9-bromo-1,2,3,4,5,6-hexahydro-1,5-methano-pyrido[1,2-a][1,5]diazocin-8-one; and, 3-benzyl-9-chloro-1,2,3,4,5,6-hexahydro-1,5-methano-pyrido[1,2-a][1,5]diazocin-8-one.

12. The compound according to claim 1 wherein said pharmaceutically acceptable acid addition salts are the salts of acids selected from the group consisting of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, maleic and mandelic acid.

13. A method for treating an addictive disorder in a mammal which comprises administering to said mammal, in need thereof, an amount of a compound of claim 1 effective in treating said disorder.

14. The method of claim 13 wherein the compound of formula I is selected from 9-morpholino-12,3,4,5,6-hexahydro-1,5-methano-pyrido[1,2a][1,5]diazocin-8-one;

9-benzylamino-1,2,3,4,5,6-hexahydro-1,5-methano-pyrido[1,2a][1,5]diazocin-8-one;

9-pyrrolidino-1,2,3,4,5,6-hexahydro-1,5-methano-pyrido[1,2a][1,5]diazocin-8-one;

9-dimethylamino-1,2,3,4,5,6-hexahydro-1,5-methano-pyrido[1,2a][1,5]diazocin-8-one;

9-acetyl-1,2,3,4,5,6-hexahydro-1,5-methano-pyrido[1,2a][1,5]diazocin-8-one;

9-(2-tetrahydrofuranyl)-1,2,3,4,5,6-hexahydro-1,5-methano-pyrido[1,2a][1,5]diazocin-8-one;

9-iodo-1,2,3,4,5,6-hexahydro-1,5-methano-pyrido[1,2a][1,5]diazocin-8-one;

9-cyano-1,2,3,4,5,6-hexahydro-1,5-methano-pyrido[1,2a][1,5]diazocin-8-one;

9-ethynyl-1,2,3,4,5,6-hexahydro-1,5-methano-pyrido[1,2a][1,5]diazocin-8-one;

9-(2-propenyl)-1,2,3,4,5,6-hexahydro-1,5-methano-pyrido[1,2a][1,5]diazocin-8-one;

9-(2-propyl)-1,2,3,4,5,6-hexahydro-1,5-methano-pyrido[1,2a][1,5]diazocin-8-one;

9-carbomethoxy-1,2,3,4,5,6-hexahydro-1,5-methano-pyrido[1,2a][1,5]diazocin-8-one;

9-carboxyaldehyde-1,2,3,4,5,6-hexahydro-1,5-methano-pyrido[1,2a][1,5]diazocin-8-one;

9-(2-methoxyphenyl)-1,2,3,4,5,6-hexahydro-1,5-methano-pyrido[1,2a][1,5]diazocin-8-one;

9-(2,6-difluorophenyl)-1,2,3,4,5,6-hexahydro-1,5-methano-pyrido[1,2a][1,5]diazocin-8-one;

9-[2-(1,1,1-trifluoromethylpropenyl)-1,2,3,4,5,6-hexahydro-1,5-methano-pyrido[1,2a][1,5]diazocin-8-one;

9-(4-methoxyphenyl)-1,2,3,4,5,6-hexahydro-1,5-methano-pyrido[1,2a][1,5]diazocin-8-one;

9-(2-ethoxy-5-methylphenyl)-1,2,3,4,5,6-hexahydro-1,5-methano-pyrido[1,2a][1,5]diazocin-8-one;

9-(2-benzofuranyl)-1,2,3,4,5,6-hexahydro-1,5-methano-pyrido[1,2a][1,5]diazocin-8-one;

9-(2-thienyl)-1,2,3,4,5,6-hexahydro-1,5-methano-pyrido[1,2a][1,5]diazocin-8-one;

9(3-thienyl)-1,2,3,4,5,6-hexahydro-1,5-methano-pyrido[1,2a][1,5]diazocin-8-one;

9-[3-(4-methylthienyl)]-1,2,3,4,5,6-hexahydro-1,5-methano-pyrido[1,2a][1,5]diazocin-8-one;

9-[2-(3-methylthienyl)]-1,2,3,4,5,6-hexahydro-1,5-methano-pyrido[1,2a][1,5]diazocin-8-one;

9-[3-(2-fluoropyridyl)]-1,2,3,4,5,6-hexahydro-1,5-methano-pyrido[1,2a][1,5]diazocin-8-one;

9-(2-pyridyl)-1,2,3,4,5,6-hexahydro-1,5-methano-pyrido[1,2a][1,5]diazocin-8-one;

9-(2-furanyl)-1,2,3,4,5,6-hexahydro-1,5-methano-pyrido[1,2a][1,5]diazocin-8-one;

9-(3-furanyl)-1,2,3,4,5,6-hexahydro-1,5-methano-pyrido[1,2a][1,5]diazocin-8-one;

9-(2-trifluoromethylphenyl)-1,2,3,4,5,6-hexahydro-1,5-methano-pyrido[1,2a][1,5]diazocin-8-one;

9-(4-trifluoromethylphenyl)-1,2,3,4,5,6-hexahydro-1,5-methano-pyrido[1,2a][1,5]diazocin-8-one;

9-phenyl-1,2,3,4,5,6-hexahydro-1,5-methano-pyrido[1,2a][1,5]diazocin-8-one;

9-(2-methylphenyl)-1,2,3,4,5,6-hexahydro-1,5-methano-pyrido[1,2a][1,5]diazocin-8-one;

9-(3-acetylphenyl)-1,2,3,4,5,6-hexahydro-1,5-methano-pyrido[1,2a][1,5]diazocin-8-one;

9-(2-chlorophenyl)-1,2,3,4,5,6-hexahydro-1,5-methano-pyrido[1,2a][1,5]diazocin-8-one;

9-(3,4-dichlorophenyl)-1,2,3,4,5,6-hexahydro-1,5-methano-pyrido[1,2a][1,5]diazocin-8-one.

9-(2-fluorophenyl)-1,2,3,4,5,6-hexahydro-1,5-methano-pyrido[1,2a][1,5]diazocin-8-one;

9-(4-fluorophenyl)-1,2,3,4,5,6-hexahydro-1,5-methano-pyrido[1,2a][1,5]diazocin-8-one;

9-(3-fluorophenyl)-1,2,3,4,5,6-hexahydro-1,5-methano-pyrido[1,2a][1,5]diazocin-8-one;

9-(3,5-difluorophenyl)-1,2,3,4,5,6-hexahydro-1,5-methano-pyrido[1,2a][1,5]diazocin-8-one;

9-(2,4-difluorophenyl)-1,2,3,4,5,6-hexahydro-1,5-methano-pyrido[1,2a][1,5]diazocin-8-one 9-(2-fluoro-4-chlorophenyl)-1,2,3,4,5,6-hexahydro-1,5-methano-pyrido[1,2a][1,5]diazocin-8-one;

9-(2-fluoro-4-methoxyphenyl)-1,2,3,4,5,6-hexahydro-1,5-methano-pyrido[1,2a][1,5]diazocin-8-one;

9-(2,5-difluorophenyl)-1,2,3,4,5,6-hexahydro-1,5-methano-pyrido[1,2a][1,5]diazocin-8-one;

9-(2-thiazoyl)-1,2,3,4,5,6-hexahydro-1,5-methano-pyrido[1,2a][1,5]diazocin-8-one;

9-chloro-1,2,3,4,5,6-hexahydro-1,5-methano-pyrido[1,2-a][1,5]diazocin-8-one;

9-flouro-1,2,3,4,5,6-hexahydro-1,5-methano-pyrido[1,2-a][1,5]diazocin-8-one;

9-ethyl-1,2,3,4,5,6-hexahydro-1,5-methano-pyrido[1,2-a][1,5]diazocin-8-one;

9-methyl-1,2,3,4,5,6-hexahydro-1,5-methano-pyrido[1,2-a][1,5]diazocin-8-one;

9-phenyl-1,2,3,4,5,6-hexahydro-1,5-methano-pyrido[1,2-a][1,5]diazocin-8-one;

9-vinyl-1,2,3,4,5,6-hexahydro-1,5-methano-pyrido[1,2-a][1,5]diazocin-8-one;

3-benzyl-9-bromo-1,2,3,4,5,6-hexahydro-1,5-methano-pyrido[1,2-a][1,5]diazocin-8-one; and 3-benzyl-9-chloro-1,2,3,4,5,6-hexahydro-1,5-methano-pyrido[1,2-a][1,5]diazocin-8-one.

15. A composition for treating an addictive disorder in a mammal comprising a pharmaceutically acceptable carrier and an amount of a compound of claim 1 effective in treating said disorder.

* * * * *

UNITED STATES PATENT AND TRADEMARK OFFICE
CERTIFICATE OF CORRECTION

PATENT NO. : 6,630,467 B2
DATED : October 7, 2003
INVENTOR(S) : Brian T. O'Neill It is certified that error appears in the above-identified patent and that said Letters Patent is hereby corrected as shown below:

<u>Title page,</u>
Item [74], *Attorney, Agent, or Firm*, replace "P.C. Richardson; S. Drouin; A.D. Joran" with -- P.C. Richardson; A.D. Joran --

Signed and Sealed this

Third Day of May, 2005

JON W. DUDAS
*Director of the United States Patent and Trademark Office*